US009688719B2

(12) United States Patent
Eldar-Finkelman et al.

(10) Patent No.: US 9,688,719 B2
(45) Date of Patent: Jun. 27, 2017

(54) GLYCOGEN SYNTHASE KINASE-3 INHIBITORS

(75) Inventors: Hagit Eldar-Finkelman, Shoham (IL); Miriam Eisenstein, Rehovot (IL)

(73) Assignees: Ramot at Tel-Aviv University Ltd., Tel-Aviv (IL); Yeda Research and Development Co. Ltd., Rehovot (IL)

( * ) Notice: Subject to any disclaimer, the term of this patent is extended or adjusted under 35 U.S.C. 154(b) by 242 days.

(21) Appl. No.: 13/982,300

(22) PCT Filed: Jan. 26, 2012

(86) PCT No.: PCT/IB2012/050376
§ 371 (c)(1),
(2), (4) Date: Jul. 29, 2013

(87) PCT Pub. No.: WO2012/101601
PCT Pub. Date: Aug. 2, 2012

(65) Prior Publication Data
US 2013/0303441 A1 Nov. 14, 2013

Related U.S. Application Data

(60) Provisional application No. 61/436,629, filed on Jan. 27, 2011.

(51) Int. Cl.
| | | |
|---|---|---|
| C07K 7/06 | (2006.01) | |
| C07K 2/00 | (2006.01) | |
| C07K 7/08 | (2006.01) | |
| C12N 9/12 | (2006.01) | |
| A61K 38/00 | (2006.01) | |

(52) U.S. Cl.
CPC .............. C07K 2/00 (2013.01); C07K 7/06 (2013.01); C07K 7/08 (2013.01); C12N 9/1205 (2013.01); C12Y 207/01037 (2013.01); A61K 38/00 (2013.01)

(58) Field of Classification Search
None
See application file for complete search history.

(56) References Cited

U.S. PATENT DOCUMENTS

| 6,780,625 | B2 | 8/2004 | Eldar-Finkelman |
| 7,378,432 | B2 | 5/2008 | Eldar-Finkelman et al. |
| 2006/0135408 | A1 | 6/2006 | Eldar-Finkelman |
| 2009/0068684 | A1* | 3/2009 | Moritz ............... C07K 16/44 435/7.23 |
| 2011/0059463 | A1 | 3/2011 | Moritz et al. |
| 2011/0150887 | A1 | 6/2011 | Rincon et al. |
| 2013/0310303 | A1 | 11/2013 | Eldar-Finkelman et al. |
| 2016/0130303 | A1 | 5/2016 | Eldar-Finkelman et al. |

FOREIGN PATENT DOCUMENTS

| WO | WO 01/49709 | 7/2001 |
| WO | WO 2004/052404 | 6/2004 |
| WO | WO 2005/000192 | 1/2005 |
| WO | WO 2012/101599 | 8/2012 |
| WO | WO 2012/101601 | 8/2012 |

OTHER PUBLICATIONS

Sugden et al., "Review: Glycogen synthase kinase 3 (GSK3) in the heart: a point of integration in hypertrophic signaling and a therapeutic target? A critical analysis", British Journal of Pharmacology, 2008, pp. S137-S153.*
Monera et al., "Relationship of Sidechain Hydrophobicity and a-Helical Propensity on the Stability of the Single-stranded Amphipathic a-Helix", Journal of Peptide Science, 1995, pp. 319-329.*
Nishikawa et al. ,"Determination of the Specific Substrate Sequence Motifs of Protein Kinase C Isozymes", The Journal of Biological Chemistry, 1997, pp. 952-960.*
Otvos et al., "Glycosylation of synthetic peptides breaks helices", Int. J. Peptide Protein Res., 1991, pp. 476-482.*
Communication Relating to the Results of the Partial International Search Dated May 30, 2012 From the International Searching Authority Re. Application No. PCT/IB2012/050373.
International Preliminary Report on Patentability Dated Aug. 8, 2013 From the International Bureau of WIPO Re. Application No. PCT/IB2012/050376.
International Preliminary Report on Patentability Dated Aug. 8, 2013 From the International Bureau of WIPO Re. Application No. PCT/IB2012/050373.
International Search Report and the Written Opinion Dated Nov. 9, 2012 From the International Searching Authority Re. Application No. PCT/IB2012/050373.
International Search Report and the Written Opinion Dated Jun. 11, 2012 From the International Searching Authority Re. Application No. PCT/IB2012/050376.
Bertrand et al. "Structural Characterization of the GSK-3? Active Site Using Selective and Non-Selective ATP-Mimetic Inhibitors", The Journal of Molecular Biology, 333: 393-407, 2003.
Chen et al. "Glycogen Synthase Kinase 3? (GSK3?) Mediates 6-Hydroxydopamine-Induced Neuronal Death", The FASEB Journal, p. 1-26, May 7, 2004.
Dajani et al. "Crystal Structure of Glycogen Synthase Kinase 3 Beta: Structural Basis for Phosphate-Primed Substrate Specificity and Autoinhibition", Cell, 105: 721-732, 2001.
Fiol et al. "Formation of Protein Kinase Regognition Sites by Covalent Modification of Substrate. Molecular Mechanism for the Synergistic Action of Casein Kinase II and Glycogen Synthase Kinase 3", The Journal of Biological Chemistry, 262(29): 14042-14048, 1987.
Ilouz et al. "Identification of Novel Glycogen Synthase Kinase-3? Substrate-Interacting Residues Suggests a Common Mechanism for Substrate Recognition", The Journal of Biological Chemistry, 281(41): 30621-30630, Oct. 13, 2006.
Ilouz et al. "New Insights Into Autoinhibition Mechanism of Glycogen Synthasc Kinase-3Beta", Journal of Molecular Biology, XP025536484, 383(5): 999-1007, Nov. 28, 2008.

(Continued)

*Primary Examiner* — Lianko Garyu

(57) ABSTRACT

Novel peptide inhibitors of GSK-3, compositions containing same and uses thereof are disclosed. The novel peptide inhibitors are substrate-competitive inhibitors and have an amino acid sequence designed so as to bind to a defined binding site subunit in GSK-3.

28 Claims, 7 Drawing Sheets
(4 of 7 Drawing Sheet(s) Filed in Color)

(56) References Cited

OTHER PUBLICATIONS

Kaidanovich-Beilin et al. "Long-Term Treatment With Novel Glycogen Synthase Kinase-3 Inhibitors Improves Glucose Homeostasis in Ob/Ob Mice: Molecular Characterization in Liver and Muscle", The Journal of Pharmacology and Experimental Therapeutics, 316(1): 17-24, 2006.
Kaidanovich-Beilin et al. "Rapid Antidepressive-Like Activity of Specific Glycogen Synthese Kinase-3 Inhibitor and Its Effect on ?-Catenin in Mouse Hippocampus", Biological Psychiatry, 55: 781-784, 2004.
Kim et al. "Essential Roles for GSK-3s and GSK-3-Primed Substrates in Neurotrophin-Induced and Hippocampal Axon Growth", Neuron, 52(6): 981-996, Dec. 21, 2006.
Kowalsman et al. "Combining Interface Core and Whole Interface Descriptors in Postscan Processing of Protein-Protein Docking Models", Proteins, 77: 297-318, 2009.
Liberman et al. "Coordinated Phosphorylation of Insulin Receptor Substrate-1 by Glycogen Synthase Kinase-3 and Protein Kinase C?II in the Diabetic Fat Tissue", American Journal of Physiology, Endocrinology and Metabolism, 294(6): E1169-E1177, 2008.
Liberman et al. "Serine 332 Phosphorylation of Insulin Receptor Substrate-1 by Glycogen Synthase Kinase-3 Attenuates Insulin Signaling", The Journal of Biological Chemistry, 280(6): 4422-4428, Feb. 11, 2005.
Licht-Murava et al. "Elucidating Substrate and Inhibitor Binding Sites on the Surface of GSK-3? and the Refinement of a Competitive Inhibitor", The Journal of Biological Chemistry, 408(2): 366-378, Apr. 25, 2011.
Palomo et al. "5-Imino-1,2,4-Thiadiazoles: First Small Molecules as Substrate Competitive Inhibitors of Glycogen Synthase Kinase 3", Journal of Medicinal Chemistry, 55(4): 1645-1661, Feb. 23, 2012.
Plotkin et al. "Insulin Mimetic Action of Synthetic Phosphorylated Peptide Inhibitors of Glycogen Synthase Kinase-3", Journal of Pharmacology and Experimental Therapeutics, 305(3): 974-980, 2003.
Rao et al. "Glycogen Synthase Kinase 3 Inhibition Improves Insulin-Stimulated Glucose Metabolism but Not Hypertension in High-Fat-Fed C57BL/6J Mice", Diabetologia, 50: 452-460, 2007.
Shapira et al. "Role of Glycogen Synthase Kinase-3Beta in Early Depressive Behavior Induced by Mild Traumatic Brain injury", Molecular and Cellular Neuroscience, 34: 571-577, 2007.
Ter Haar et al. "Structure of GSK-3 Beta Reveals a Primed Phosphorylation Mechanism", Nature Structural Biology, 8(7): 593-596, 2001.
Woodgett et al. "Multisite Phosphorylation of Glycogen Synthase. Molecular Basis for the Substrate Specificity of Glycogen Synthase Kinase-3 and Casein Kinase-II (Glycogen Synthase Kinase-5)", Biochimica et Biophysica Acta, 788(3): 339-347, Aug. 14, 1984.
Communication Pursuant to Article 94(3) EPC Dated Mar. 18, 2015 From the European Patent Office Re. Application No. 12705426.0.
Official Action Dated Apr. 27, 2015 From the US Patent and Trademark Office Re. U.S. Appl. No. 13/981,668.
Czernik et al. "Production of Phosphorylation State-Specific Antibodies", Methods in Enzymology, XP002926234, 201: 264-283, 1991.
Donella-Deana et al. "Dephosphorylation of Phosphopeptides by Calcineurin (Protein Phosphatase 2B)", European Journal of Biochemistry, 219(1-2): 109-117, 1994.
Otvos Jr. et al. "Glycosylation of Synthetic Peptides Breaks Hcliccs. Phosphorylation Results in Distorted Structure", International Journal of Peptide and Protein Research, 38: 476-482, 1991.
Titanji et al. "Activity of Rat-Liver Phosphoprotein Phosphatase on Phosphopeptides Formed in the Cyclic AMP-Dependent Protein Kinase Reaction", FEBS Letters, XP025615084, 78(1): 86-90, Jun. 1977.
Titanji et al. "Phosphopeptide Substrates of a Phosphoprotein Phosphatase From Rat Liver", The Journal of Biological Chemistry, 255(23): 11339-11343, Dec. 10, 1980.
Official Action Dated Oct. 8, 2014 From the US Patent and Trademark Office Re. U.S. Appl. No. 13/981,668.
Communication Pursuant to Article 94(3) EPC Dated Oct.13, 2016 From the European Patent Office Re. Application No. 12704133.3.

\* cited by examiner

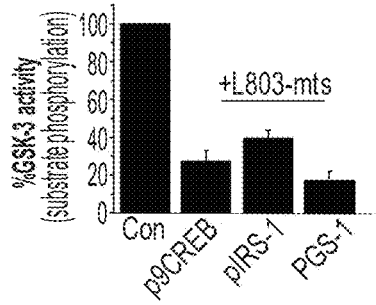 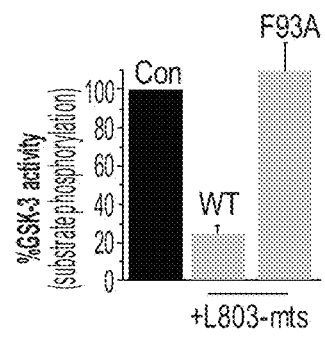 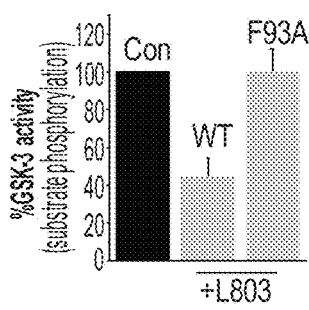
FIG. 2A  FIG. 2B  FIG. 2C
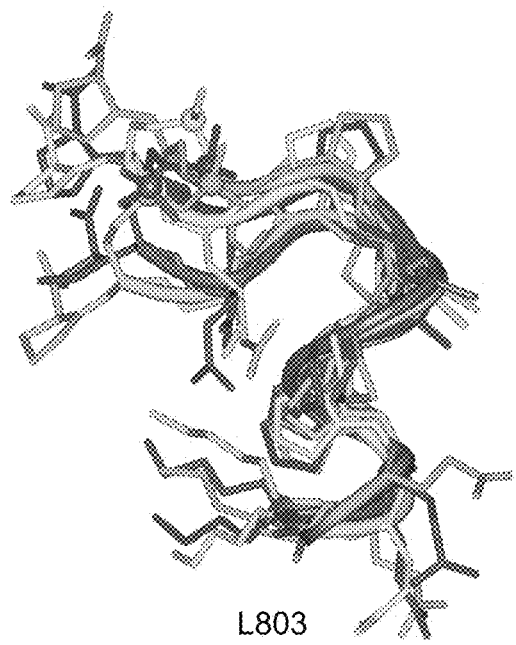
FIG. 3

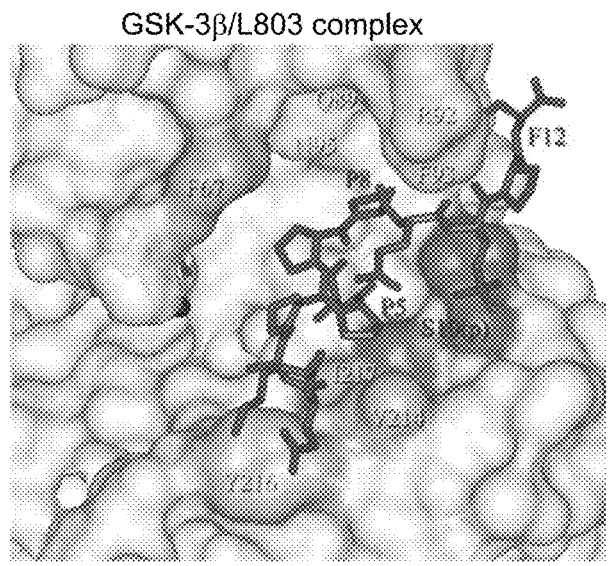
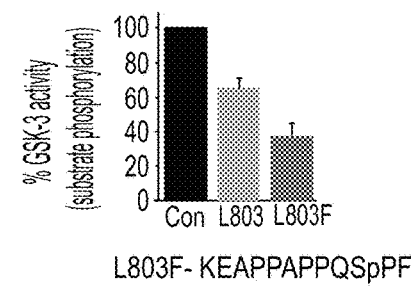
FIG. 6A  FIG. 6B
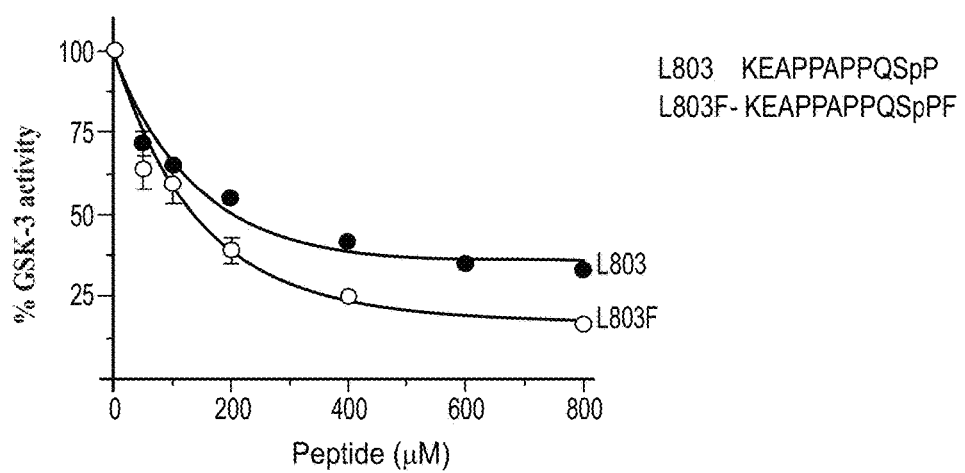
FIG. 7

GLYCOGEN SYNTHASE KINASE-3 INHIBITORS

RELATED APPLICATIONS

This application is a National Phase of PCT Patent Application No. PCT/IB2012/050376 having International filing date of Jan. 26, 2012, which claims the benefit of priority under 35 USC §119(e) of U.S. Provisional Patent Application No. 61/436,629 filed on Jan. 27, 2011. The contents of the above applications are all incorporated by reference as if fully set forth herein in their entirety.

SEQUENCE LISTING STATEMENT

The ASCII file, entitled 56957SequenceListing.txt, created on Jul. 1, 2013, comprising 30,304 bytes, submitted concurrently with the filing of this application is incorporated herein by reference.

FIELD AND BACKGROUND OF THE INVENTION

The present invention, in some embodiments thereof, relates to novel glycogen synthase kinase-3 (GSK-3) inhibitors and, more particularly, but not exclusively, to novel substrate-competitive peptide inhibitors of glycogen synthase kinase-3 (GSK-3) and to the use of such peptide inhibitors in the treatment of biological conditions associated with GSK-3 activity.

Protein kinases and phosphorylation cascades are essential for life and play key roles in the regulation of many cellular processes including cell proliferation, cell cycle progression, metabolic homeostasis, transcriptional activation and development. Aberrant regulation of protein phosphorylation underlies many human diseases, and this has prompted the development and design of protein kinase inhibitors. Most of the protein kinase inhibitors developed so far compete with ATP for its binding site. These inhibitors, although often very effective, generally show limited specificity due to the fact that the ATP binding site is highly conserved among protein kinases.

Other sites, such as the substrate's binding site, show more variability in their shape and amino acid compositions and may serve as favorable sites for drug design. Understanding of substrate recognition and specificity is thus essential for development of substrate competitive inhibitors. This knowledge, however, is limited by the scarce amount of structural data regarding substrate binding.

Glycogen synthase kinase-3 (GSK-3) is a constitutively active serine/threonine kinase that modulates diverse cellular functions including metabolism, cell survival and migration, neuronal signaling and embryonic development. Deregulation of GSK-3 activity has been implicated in the pathogenesis of human diseases such as, for example, type-2 diabetes, neurodegenerative disorders and psychiatric disorders. Selective inhibition of GSK-3 is thought to be of therapeutic value in treating these disorders [Bhat et al. (2004). J. Neurochem. 89, 1313-7; Cohen, P. & Goedert, M. (2004). Nat. Rev. Drug Discov. 3, 479-87; Meijer et al. (2004) Trends Pharmacol Sci 25, 471-80; Eldar-Finkelman et al. Biochim Biophys Acta 1804, 598-603; Martinez, A. & Perez, D. 1. (2008) J. Alzheimers Dis. 15, 181-91].

Recently, it has been found that GSK-3 is also involved in the pathogenesis of cardiovascular diseases [Cheng et al. 2010 J. Mol. Cell Cardiol, in press; Kerkela et al. 2008, J. Clin. Invest. 118:3609-18], of malaria and trypanosomiasis [Droucheau et al. 2004, BBRC, 1700:139-140; Ojo et al. 2008, Antimicrob Agents Chemother, 37107-3717], and in stem cell maintenance or differentiation [Wray et al. 2010 Biochem Soc Trans 1027-32].

In view of the wide implication of GSK-3 in various signaling pathways, development of specific inhibitors for GSK-3 is considered both promising and important regarding various therapeutic interventions as well as basic research. Some mood stabilizers were found to inhibit GSK-3. However, while the inhibition of GSK-3 both by lithium chloride (LiCl) (WO 97/41854) and by purine inhibitors (WO 98/16528) has been reported, these inhibitors are not specific for GSK-3. In fact, it was shown that these drugs affect multiple signaling pathways, and inhibit other cellular targets, such as inositol monophosphatase (IMpase) and histone deacetylases.

Similarly, an engineered cAMP response element binding protein (CREB), a known substrate of GSK-3, has been described (Fiol et al, 1994), along with other potential GSK-3 peptide inhibitors (Fiol et al, 1990). However, these substrates also only nominally inhibit GSK-3 activity.

Other GSK-3 inhibitors have been reported. Two structurally related small molecules SB-216763 and SB-415286 (Glaxo SmithKline Pharmaceutical) that specifically inhibited GSK-3 were developed and were shown to modulate glycogen metabolism and gene transcription as well as to protect against neuronal death induced by reduction in PI3 kinase activity (Cross et al., 2001; Coghlan et al., 2000). Another study indicated that Induribin, the active ingredient of the traditional Chinese medicine for chronic myelocytic leukemia, is a GSK-3 inhibitor. However, Indirubin also inhibits cyclic-dependent protein kinase-2 (CDK-2) (Damiens et al., 2001). These GSK-3 inhibitors are ATP competitive and were identified by high throughput screening of chemical libraries. It is generally accepted that a major drawback of ATP-competitive inhibitors is their limited specificity (see, for example, Davies et al., 2000).

The present inventors have previously reported of a novel class of substrate competitive inhibitors for GSK-3 [Plotkin et al. (2003) J. Pharmacol. Exp. Ther., 974-980], designed based on the unique substrate-recognition motif of GSK-3 that includes a phosphorylated residue (usually serine) in the context of SXXXS(p) (SEQ ID NO:3) (where S is the target serine, S(p) is phosphorylate serine and X is any amino acid) [Woodgett & Cohen (1984) Biochim. Biophys. Acta. 788, 339-47; Fiol et al. (1987) J. Biol. Chem. 262, 14042-8]. Structural studies of GSK-3β identified a likely docking site for the phosphorylated residue; it is a positively charged binding pocket composed of Arg 96, Arg 180, and Lys 205 [Dajani et al. (2001) Cell 105, 721-32; ter Haar et al. (2001) Nature Structural Biology 8, 593-6].

The short phosphorylated peptides patterned after the GSK-3 substrates behaved as substrate competitive inhibitors (Plotkin et al., 2003, supra), with the L803 peptide having an amino acid sequence as set forth in SEQ. ID NO:4, KEAPPAPPQS(p)P, derived from the substrate heat shock factor-1 (HSF-1) showing the best inhibition activity of those evaluate. An advanced version of L803, the cell permeable peptide L803-mts, was shown to promote beneficial biological activities in conditions associated with diabetes, neuron growth and survival, and mood behavior [Kaidanovich-Beilin & Eldar-Finkelman (2005) J. Pharmacol. Exp. Ther. 316:17-24; Rao et al. (2007) Diabetologia 50, 452-60; Kim et al. (2006) Neuron 52, 981-96; Chen et al. (2004) Faseb J 18, 1162-4; Kaidanovich-Beilin et al. (2004) Biol. Psychiatry.55:781-4; Shapira et al. (2007) Mol. Cell Neurosci. 34, 571-7].

While further focusing on substrate recognition of GSK-3, three positions in the vicinity of the catalytic site (Phe67 in the P-loop, Gln89 and Asn95) were identified as important for GSK-3 substrates binding [Ilouz et al. (2006) *J. Biol. Chem.* 281, 30621-30].

Additional background art includes U.S. Pat. Nos. 6,780,625 and 7,378,432; WO 2004/052404 and WO 2005/000192; WO 01/49709; Liberman, Z. & Eldar-Finkelman, H. (2005) *J. Biol. Chem.* 280, 4422-8; Liberman et al. (2008) *Am. J. Physiol. Endocrinol. Metab.* 294, E1169-77; Bertrand et al. (2003) *J. Mol. Biol.* 333, 393-407; Licht-Murava et al., *J. Mol. Biol.* (2011) 408, 366-378; and Palomo et al. *J. Med. Chem.* (2012) as published on wwwdotpubsdotacsdotorg as "Just Accepted Manuscript" on Jan. 18, 2012.

SUMMARY OF THE INVENTION

According to an aspect of some embodiments of the present invention there is provided a peptide having the amino acid sequence:

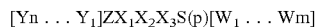

wherein, m equals 1 or 2;

n is an integer from 3 to 7, such that the polypeptide consists of 10 to 13 amino acid residues;

S(p) is a phosphorylated serine residue or a phosphorylated threonine residue;

Z is any amino acid residue excepting serine residue or threonine residue; and $X_1$-$X_3$ and $Y_1$-$Y_n$ are each independently any amino acid residue; and Each of $W_1$ and $W_m$ is any amino acid residue provided that at least one of $W_1$ and $W_m$ is an amino acid residue that is capable of interacting with a phenylalanine residue at the Q89-N95 subunit (SEQ. ID NO:2) a binding site of a GSK-3 enzyme.

According to some embodiments of the invention, the phenylalanine residue at the subunit is at position 93 of a GSK-3 enzyme.

According to some embodiments of the invention, at least one of $W_1$ and $W_m$ is an aromatic amino acid residue.

According to some embodiments of the invention, at least one of $W_1$ and $W_m$ is a phenylalanine residue.

According to some embodiments of the invention, m is 2.

According to some embodiments of the invention, $W_2$ is phenylalanine.

According to some embodiments of the invention, $W_1$ is proline.

According to some embodiments of the invention, S(p) is a phosphorylated serine.

According to some embodiments of the invention, Z is an alanine residue.

According to some embodiments of the invention, $X_1$ and $X_2$ are each a proline residue.

According to some embodiments of the invention, $X_3$ is a glutamine residue.

According to some embodiments of the invention, n is 5.

According to some embodiments of the invention, $Y_1$-$Y_5$ has the amino acid sequence Lys-Glu-Ala-Pro-Pro, as set forth in the SEQ ID NO. 17.

According to some embodiments of the invention, the peptide has an amino acid sequence as set forth in SEQ ID NO:11.

According to some embodiments of the invention, the peptide as described herein further comprises a hydrophobic moiety attached thereto.

According to some embodiments of the invention, the hydrophobic moiety is selected from the group consisting of a fatty acid and a fatty acid attached to an amino acid residue.

According to some embodiments of the invention, the peptide has an amino acid sequence as set forth in SEQ ID NO:12.

According to an aspect of some embodiments of the present invention there is provided a pharmaceutical composition comprising, as an active ingredient, the peptide as described herein, and a pharmaceutically acceptable carrier.

According to some embodiments of the invention, the pharmaceutical composition is packaged in a packaging material and identified in print, on or in the packaging material, for use in the treatment of a biological condition associated with GSK-3 activity.

According to an aspect of some embodiments of the present invention there is provided a peptide as described herein, for use in inhibiting an activity of GSK-3.

According to an aspect of some embodiments of the present invention there is provided a peptide as described herein for use in the treatment of a biological condition associated with GSK-3 activity.

According to an aspect of some embodiments of the present invention there is provided a method of inhibiting an activity of GSK-3, the method comprising contacting cells expressing GSK-3 with an effective amount of the peptide as described herein.

According to some embodiments of the invention, the activity is a phosphorylation activity and/or an autophosphorylation activity.

According to an aspect of some embodiments of the present invention there is provided a method of treating a biological condition associated with GSK-3 activity, the method comprising administering to a subject in need thereof a therapeutically effective amount of the peptide as described herein.

According to an aspect of some embodiments of the present invention there is provided a use of the peptide as described herein in the manufacture of a medicament for treating a biological condition associated with GSK-3 activity.

According to some embodiments of the invention, the biological condition is selected from the group consisting of obesity, non-insulin dependent diabetes mellitus, an insulin-dependent condition, an affective disorder, a neurodegenerative disease or disorder, a psychotic disease or disorder, a cardiovascular disease or disorder, a condition associated with a pathogenic parasite, and a condition treatable by stem cell transplantation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 4:
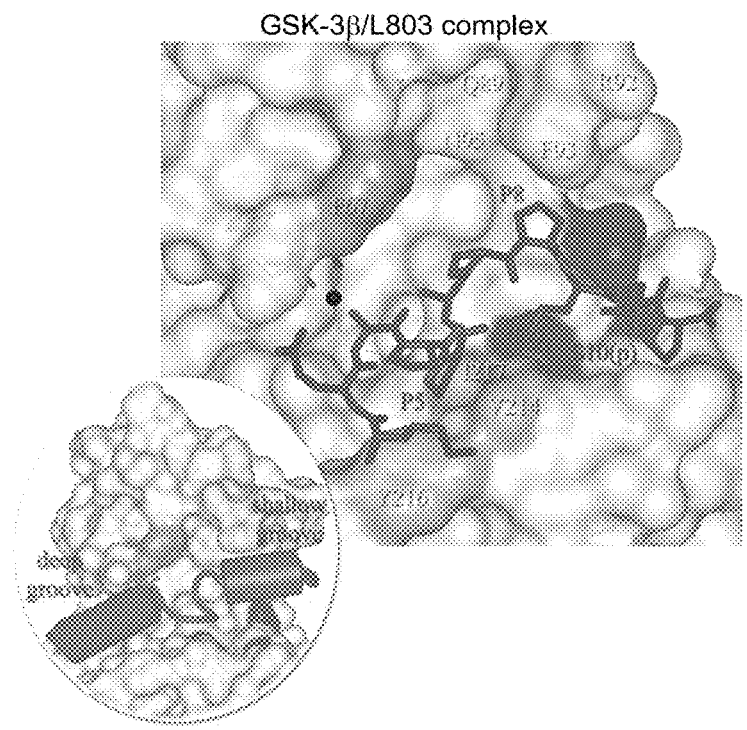
Figure 5:
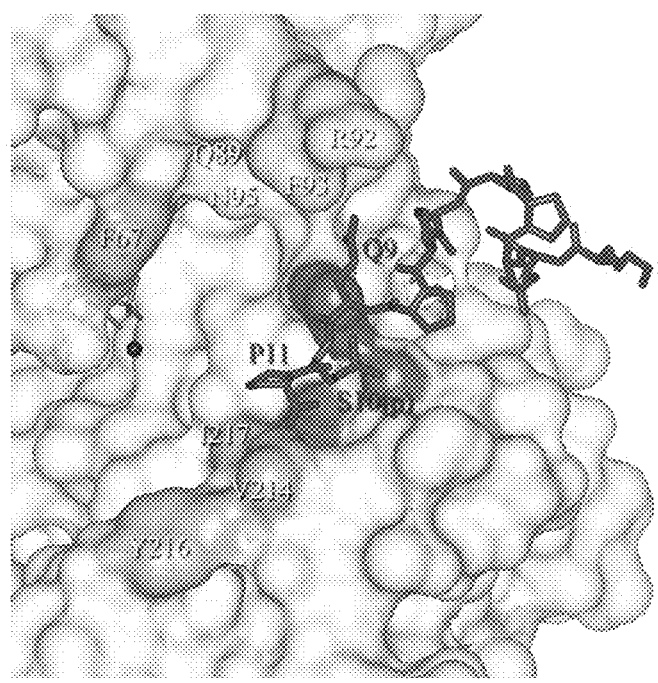
Figure 8:
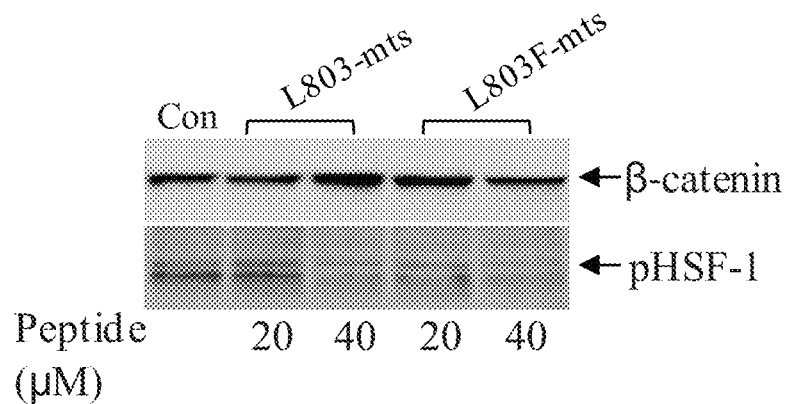
Figure 9:
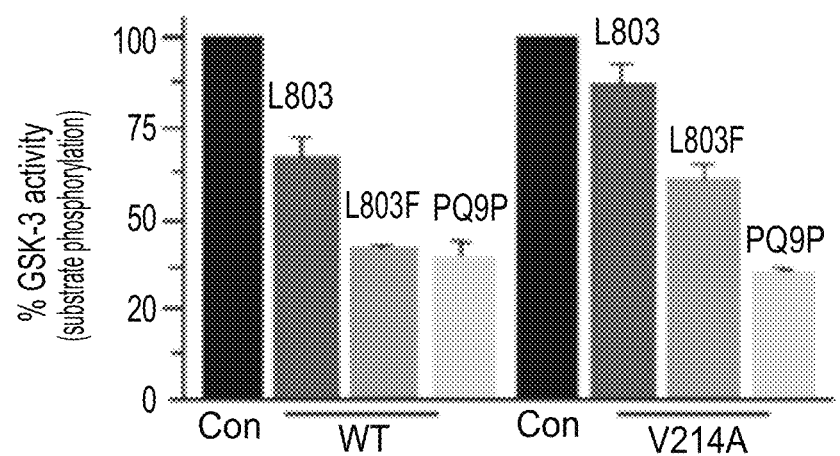

FIGS. 1A-H present the cavity in GSK-3β bordered by the P-loop and by loop 89-95 having an amino acid sequence as set forth in SEQ ID NO:2 where a variety of amino acid side chains can bind (FIG. 1A), the modifications made to the 89-95 containing binding subsite of GSK-3β having an amino acid sequence as set forth in SEQ ID NO:18 (FIG. 1B), Western Blot analyses of the expression of GSK-3β WT SEQ ID NO:1, and GSK-3β mutants D90A SEQ ID NO:6), K91A (SEQ ID NO:7), R92A (SEQ ID NO:8), F93A (SEQ ID NO:9), K94A (SEQ ID NO:10) (FIG. 1C), a bar graph showing the phosphorylation of peptide substrates by the F93A mutant (SEQ ID NO:9) (FIG. 1D); and data showing phosphorylation of substrate proteins by F93A (SEA ID NO:9) in cells (FIGS. 1E-1H;

FIGS. 2A-C are bar graphs showing that L803-mts is a (SEQ ID NO:5) is a substrate competitive inhibitor of purified GSK-3β (FIG. 2A) and that both L803-mts (SEQ ID NO:5) and L803 (SEQ ID NO:4) do not inhibit substrate phosphorylation by F93A (SEQ ID NO:9) (FIGS. 2B and 2C, respectively);

FIG. 3 presents five snapshots from the MD trajectory of L803 (SEQ ID NO:4) in water showing the span of conformations in the largest cluster (the carbonyl oxygen atoms were omitted for clarity and the phosphorous atoms are shown as a sphere);

FIG. 4 presents a representative model of the interaction between L803 (SEQ ID NO:4) and GSK-3β, showing that L803 (SEQ ID NO:4) resides near the positive phosphate binding cavity, near Phe 93, and near the hydrophobic surface patch formed by the side chains of Val 214, Tyr 216 and Ile 218, and further presents the deep and shallow grooves where the substrate pCREB (SEQ ID NO:14) (red) was predicted to bind according to previous studies (inset);

FIG. 5 presents a representative structure from the largest cluster in the MD trajectory of a simulation that started with L803 (SEQ ID NO:4) in the shallow groove, showing that L803 (SEQ ID NO:4) does not make contacts with Phe 93;

FIGS. 6A-B present a representative model of the interaction between L803F (SEQ ID NO:11) and GSK-3β (SEQ ID NO:1), showing that the binding geometry of L803F (SEQ ID NO:11) is similar to that of L803 (SEQ ID NO:4) but additional contacts with F93 are formed (FIG. 6A) and a bar graph showing the improved inhibition of GSK-3 activity by L803F (SEQ ID NO:11) (FIG. 6B);

FIG. 7 presents comparative plots further demonstrating the improved inhibition activity of L803F having an amino acid sequence as set forth in SEQ ID NO:11, compared to L803 having an amino acid sequence as set forth in SEQ ID NO:4;

FIG. 8 presents Western blot analysis presenting the inhibition of cellular GSK-3 as reflected by β-catenin levels and by phosphorylation of HSF-1(Ser301), in the presence of L803F-mts (SEQ ID NO:12) as compared to L-802-mts (SEQ ID NO:5) and to non-treated cells; and FIG. 9 is a bar graph demonstrating an impaired inhibition activity of the GSK-3β V214A mutant (SEQ ID NO:13), compared to wild-type GSK-3 (SEQ ID NO:1), by L-803F (SEQ ID NO:11).

DESCRIPTION OF SPECIFIC EMBODIMENTS OF THE INVENTION

The present invention, in some embodiments thereof, relates to novel glycogen synthase kinase-3 (GSK-3) inhibitors and, more particularly, but not exclusively, to novel substrate-competitive peptide inhibitors of glycogen synthase kinase-3 (GSK-3) and to the use of such peptide inhibitors in the treatment of biological conditions associated with GSK-3 activity.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have previously described that peptides designed after the recognition motif of a GSK-3 substrate are useful as GSK-3 substrate competitive inhibitors. See, for example, WO 01/49709 and U.S. Patent Application No. 20020147146, which are incorporated by reference as if fully set forth herein.

These peptides were designed further to the findings that GSK-3 has a unique recognition motif, and thus that short peptides which are designed with reference to this motif are highly specific GSK-3 inhibitors.

The unique recognition motif of GSK-3, as set forth in SEQ ID NO:3, is $SX_1X_2X_3S(p)$, where S is serine or threonine, each of $X_1$, $X_2$ and $X_3$ is any amino acid, and $S(p)$ is phosphorylated serine or phosphorylated threonine. Based on this recognition motif, a set of peptides, which differ one from another in various parameters (e.g., length, phosphorylation, sequence, etc.) have been designed, synthesized and were tested for their activity as either substrates or inhibitors of GSK-3.

Based on these experiments, a number of features, which would render a peptide an efficient GSK-3 inhibitor, have been determined. For example, it was found that the phosphorylated serine or threonine residue in the motif is necessary for binding. Without this residue, the peptide will neither be a substrate nor an inhibitor. It was further determined that a serine (or threonine) residue upstream of the phosphorylated serine (or threonine) residue separated by three additional residues renders the peptide a GSK-3 substrate, whereas replacement of this serine or threonine residue by any other amino acid, preferably alanine, converts the substrate to a GSK-3 inhibitor. It was further found that the number of the additional residues, outside the recognition motif, affect the inhibition potency of the peptide, such that, for example, a total number of between 7 and 50, preferably, between 7 and 20, more preferably between 10 and 13 amino acid residues, is preferable.

Hence, it was previously described that peptides having the general amino acid sequence denoted herein as general sequence I*:

$$[Y_n \ldots Y_1]ZX_1X_2X_3S(p)[W_1 \ldots W_m] \tag{I*}$$ 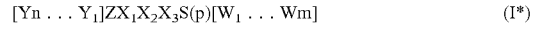

wherein m equals 1 or 2; n is an integer from 1 to 50; S(p) is a phosphorylated serine residue or a phosphorylated threonine residue; Z is any amino acid residue excepting serine residue or threonine residue; and $X_1$, $X_2$, $X_3$, $Y_1$-$Y_n$ and $W_1$-$W_m$ are each independently any amino acid residue, are highly efficient and specific inhibitors of GSK-3. See, for example, U.S. Pat. Nos. 6,780,625 and 7,378,432; WO 2004/052404 and WO 2005/000192; WO 01/49709, which are incorporated by reference as if fully set forth herein. It is noted that since these previously described inhibitors were designed so as to modify an amino acid sequence of known GSK-3 substrates, the nature of the amino acid residues presented by variables $X_1$, $X_2$, $X_3$, $Y_1$-Yn and $W_1$-Wm in the amino acid sequence I* was typically defined per the corresponding residues in the known GSK-3 substrate, namely, $X_1$, $X_2$, $X_3$ were the same as correspond amino acid residues between a serine and a phosphorylated serine in a known GSK-3 substrate, $Y_1$-Yn were the same as the amino acid residues upstream the serine residue, and $W_1$-Wm were the same as the amino acid residues downstream the phosphorylated serine or threonine residue of a known GSK-3 substrate.

It was further described that preferred peptides are those having an alanine residue at the Z position, having any amino acid residue excepting glutamic acid as $X_3$, and/or having between 7 and 20 amino acid residues, preferably between 10 and 13 amino acid residues and more preferably between 10 and 11 amino acid residues.

It was further described that a conjugate of the peptide inhibitor described above and a hydrophobic moiety, such as a fatty acid, attached at the N-terminus of the polypeptide, exerts higher inhibition of GSK-3 activity (see, for example, WO 2004/052404).

These peptides were defined as substrate competitive inhibitors.

As is well known in the art, substrate competitive enzyme inhibitors act by binding to the catalytic domain of an enzyme, thus reducing the proportion of enzyme molecules that are bound to the enzyme during the catalytic process.

While recognizing that the development of substrate competitive inhibitors depends on a molecular understanding of substrate recognition of protein kinases, efforts have been made in order to define the catalytic binding sites of GSK-3. Thus, Phe67, Gln89 and Asn95 within GSK-3β have been reported to play a role in substrates' binding [see, for example, Ilouz et al., 2006, supra), and a cavity bordered by loop 89-QDKRFKN-95 (as set forth in SEQ ID NO:2), located in the vicinity of the GSK-3β catalytic core, has been identified as a promiscuous substrate binding subsite (see, FIG. 1A).

The present inventors have further explored the role of the 89-95 loop (SEQ ID NO:2) in GSK-3β substrate binding. Each of the amino acid residues within this segment was individually mutated to alanine (see, FIG. 1B). The generated mutants are denoted herein D90A, K91A, R92A, F93A, K94A, and are represented as comprising at positions 89-95 an amino acid sequence as set forth in SEQ ID NOS:6-10, respectively. These mutants were transiently expressed in HEK-293 cells. These mutants were considerably expressed, and, similarly to the wild-type (WT) GSK-3β (SEQ ID NO :1), were phosphorylated at Tyr216 (see, FIG. 1C, lower panel), indicating that their catalytic activity was not impaired by the mutation (since phosphorylation at Tyr216 is indicative of an auto-phosphorylation process).

The generated GSK-3β mutants (SEQ ID NOS:6-10) were tested in in vitro kinase assays with known GSK-3 substrates. The mutation at Phe93 was found to exhibit the most pronounced effect for all of tested substrates, reducing the kinase ability to phosphorylate the substrate by more than 50% (see, Table 1 hereinbelow and FIG. 1D), indicating that this position is important for substrate binding, as previously found for Gln 89 and Asn 95. Phe93 is located at the center of the 89-95 loop (SEQ ID NO:2) , it is highly exposed (81% solvent accessibility) and it faces the substrate binding subsite, facilitating contacts with a variety of residues (see, FIG. 1A). Further studies substantiated the findings that Phe93 interacts with GSK-3 substrates in cellular conditions (see, FIGS. 1E-1H). These data were in agreement with the computational modeling. The role of Phe93 and other amino acids within the 89-95 loop (SEQ ID NO:2) was tested also by determining the inhibitory activity of the previously described substrate competitive inhibitors L803 (KEAPPAPPQS(p)P; see, (SEQ ID NO:4) and its cell permeable variant L803-mts (see, SEQ ID NO:5). The results indicated that both L803-mts (SEQ ID NO:5) and L803 (SEQ ID NO:4) did not inhibit the F93A mutated enzyme (SEQ ID NO:9) (see, FIGS. 3B and 3C), yet inhibited all other mutants, thus further substantiating the role of Phe93 as a most important binding position, and the role of hydrophobic interactions as promoting inhibition of GSK-3.

Since L803 (SEQ ID NO:4) is rather rigid, predicting of its binding modes is enabled. Thus, rigid body docking of the modeled L803 (SEQ ID NI:4) to GSK-3β (SEQ ID NO:1) was executed with the geometric-electrostatic-hydrophobic version of MolFit followed by filtering based on statistical propensity measures and solvation energy estimates, and has provided further understanding on the binding of the inhibitor.

Since L803 (SEQ ID NO:4) is rather rigid, predicting of its binding modes is enabled. Thus, rigid body docking of the modeled L803 (SEQ ID NO:4) to GSK-3β (SEQ ID NO:1) was executed with the geometric-electrostatic-hydrophobic version of MolFit followed by filtering based on statistical propensity measures and solvation energy estimates, and has provided further understanding on the binding of the inhibitor.

As shown in FIG. 4, the L803 binding model shows a contact between GSK-3 Phe93 and Pro 8 and to a lesser extent Pro 11 of L803 (SEQ ID NO:4).

Based on these data, the present inventors have envisioned that an inhibitor that exhibits additional contacts with Phe93 would perform better. MD simulations with an exemplary such variant of L803, denoted herein L803F (see, SEQ ID NO:11), in which a Phe residue was added at the C-terminus of L-803, indeed showed that it interacts extensively with Phe 93 via its Pro8 and Phe12, and with the hydrophobic surface patch of GSK-3β (see, FIG. 6A).

In vitro kinase assays showed that the exemplary newly designed peptide, L803F (SEQ ID NO:11), has improved inhibition ability by about 50% relatively to L803 (SEQ ID NO:4) (see, FIGS. 6-8). Further assays showed that L803F (SEQ ID NO:11) also interacts with the hydrophobic surface patch which includes Val214 (see, FIG. 9).

Thus, the studies presented herein indicate that a putative substrate competitive inhibitor of GSK-3 should be enriched with amino acid residues that are capable of interacting with the Phe93 residue, or with an equivalent amino acid thereof, in a GSK-3 enzyme, via hydrophobic viand/or aromatic interactions.

As used herein throughout, "GSK-3 enzyme", which is also referred to herein simply as GSK-3, describes a polypeptide having an amino acid sequence of a known GSK-3 family member (e.g., GSK-3α or GSK-3β). Unless otherwise indicated, this term refers to a wild-type GSK-3 enzyme. A GSK-3 enzyme is identified by the EC number EC 2.7.11.26. While the amino acid of GSK-3 is highly conserved, a wild-type GSK-3 can be GSK-3 of a mammal (e.g., human) or of any other organism, including microorganisms. An amino acid sequence of an exemplary GSK-3, human GSK-3β is set forth in SEQ ID NO:1. A GSK-3 enzyme as used herein is homologous to SEQ ID NO:1 by at least 50%, at least 60%, at least 70%, at least 80%, at least 90% or can be 100 homologous.

By "wild-type" it is meant that the typical form of the enzyme as it occurs in nature, e.g., in an organism. A wild-type GSK-3 enzyme encompasses both enzymes isolated from an organism, chemically synthesized enzymes and recombinantly prepared enzymes.

The present inventors have thus designed novel peptides, which are based on the a recognition motif of a GSK-3 substrate, and are further designed to feature defined characteristics which provide for increased interaction of the peptide with the catalytic binding site of GSK-3, and particularly with Phe93.

Thus, newly designed peptides are disclosed herein. These peptides comprise an amino acid sequence which is derived from a recognition motif of GSK-3, as described herein, and are further designed so as to include an aromatic amino acid residue that would interact with the Phe93 coordinate within the catalytic core of a GSK-3 enzyme.

In some embodiments, the newly designed peptides are collectively represented by the amino acid sequence I as follows:

$$[Y_n \ldots Y_1]ZX_1X_2X_3S(p)[W_1 \ldots W_m] \qquad (I)$$

wherein, m equals 1 or 2;

n is an integer from 3 to 7 (i.e., equals 3, 4, 5, 6 or 7), such that said polypeptide consists of 10 to 13 amino acid residues;

S(p) is a phosphorylated serine residue or a phosphorylated threonine residue;

Z is any amino acid residue excepting serine residue or threonine residue;

$X_1$-$X_3$ and $Y_1$-$Y_n$ are each independently any amino acid residue; and $W_1$ and $W_m$ are each independently any amino acid residue, provided that at least one of $W_1$ and $W_m$ is an amino acid residue that is capable of interacting with a phenylalanine residue or an equivalent thereof at position 93 of a GSK-3 enzyme.

The polypeptides described herein can be considered as sequenced based on a GSK-3 substrate (e.g., CREB or HSF-1), while maintaining the identified recognition motif of GSK-3 described hereinabove (see, SEQ ID NO:3), which includes phosphorylated serine or threonine residue, and while replacing the serine or threonine that is at the fourth position upstream of the phosphorylated serine or threonine, and further while introducing, downstream of the phosphorylated serine or threonine, an amino acid residue that may improve the interaction of the polypeptide with the Q89-N95 binding site of GSK-3.

The phrase "natural GSK-3 substrate" or "known GSK-3 substrate" describes any peptide (or protein) which is known to be phosphorylated by GSK-3 in a biological system. By "biological system" it is meant a system of any living species including, for example, vertebrates, poultry, mammals, human beings and microorganisms, including unicellular organisms. Representative examples of natural GSK-3 substrates include, but are not limited to, HSF-1, pIRS-1, p9CREB, pGS-1, phosphorylated peptides derived from the insulin receptor substrate-1 (IRS-1) [see, for example, Liberman and Eldar-Finkelman (2005) supra], cAMP responsive element binding protein (CREB), and glycogen synthase, some of which are set forth herein as having SEQ ID NOS:14-16.

It is expected that during the life of a patent maturing from this application additional relevant GSK-substrates will be identified and the scope of the term "natural GSK-3 substrate" is intended to include all such new substrates a priori.

Thus, the polypeptides described herein were designed following further studies that were conducted in order to better define the binding site subunit in GSK-3, as delineated in Example 1 hereinafter. In these studies, it was uncovered that a phenylalanine residue at position 93 within the Q89-N95 loop in GSK-3 participates in the substrate binding of the enzyme. It was thus postulated and indeed demonstrated (both computationally and experimentally) that introducing an amino acid residue for interacting with this Phe 93, downstream of the phosphorylated serine or threonine, will result in improved substrate competitive inhibition.

Amino acids that can interact with a phenylalanine residue include, but are not limited to, hydrophobic amino acids.

The term "hydrophobic", as used herein with reference to an amino acid or any other substance or moiety describes a feature of the substance that renders its solubility in water lower than its solubility in hydrophobic organic solvents.

The term "hydrophobic" thus often translates into values such as Log P, which describes the partition coefficient of a substance between an aqueous phase (water) and an oily phase (1-octanol).

According to some embodiments of the present invention, a hydrophobic amino acid has a LogP value that is higher (i.e., less negative) than −3, or higher than −2.9, or higher than −2.8, or higher than −2.7, or higher than −2.6, or even higher than −2.5.

Exemplary hydrophobic amino acids include, but are not limited to, glycine, alanine, leucine, isoleucine, valine, proline, phenylalanine, methionine, cysteine and tryptophan.

According to some embodiments, amino acids that can interact with a phenylalanine residue include, but are not limited to, aromatic amino acids.

Aromatic amino acids are amino acids that have a side chain that comprises an aryl or a heteroaryl, as these terms are defined herein.

Aromatic amino acids can interact with a phenylalanine residue via, for example, aromatic pi-stacking, herringbone-like interactions, and other aromatic and/or hydrophobic interactions.

Exemplary naturally occurring aromatic amino acids that are suitable for use in the context of the present embodiments include phenylalanine, tyrosine and tryptophan. However, any amino acid with an aromatic side chain is contemplated.

In some embodiments, at least one of $W_1$ and $W_m$ is phenylalanine.

In some embodiments, m is 2, and at least one of $W_1$ and $W_2$ is phenylalanine.

In some embodiments, $W_2$ is phenylalanine.

In some embodiments, $W_1$ is proline and $W_2$ is phenylalanine.

In some embodiments, S(p) is a phosphorylated serine.

In some embodiments, Z is an alanine residue, although other amino acids are also contemplated for this position.

In some embodiments, n is 5, such that the peptide comprises an amino acid sequence as described herein, in which upstream to Z there are amino acid residues denoted as $Y_1$-$Y_5$.

In some embodiments, when the peptide is designed after the substrate HSF-1, $Y_1$-$Y_5$ has the amino acid sequence Lys-Glu-Ala-Pro-Pro as set forth in SEQ ID NO. 17). However, any other sequence of amino acid residues can be includes within the amino acid residues upstream to Z.

In some embodiments, $X_1$ and $X_2$ are each a proline residue, thus providing a rigid and hydrophobic nature to the peptide. Any other amino acid residue is also contemplated for each of these positions.

In some embodiments, $X_3$ is a non-hydrophobic amino acid residue. In some embodiments, $X_3$ is a polar amino acid residue.

In some embodiments, $X_3$ is a glutamine residue, although any other amino acid residue is also contemplated for this position.

In some embodiments, n is 5.

In some embodiments, $Y_1$-$Y_5$ has the amino acid sequence Lys-Glu-Ala-Pro-Pro as set forth in SEQ ID NO. 17.

In other embodiments, $Y_3$-$Y_5$ are each a hydrophobic amino acid residue (as defined herein, e.g., proline and/or alanine), and at least one of $Y_1$ and $Y_2$ is a hydrophobic amino acid residue (as defined herein, e.g., proline or alanine).

An exemplary peptide according to some embodiments of the present invention has the following amino acid sequence:

Lys-Glu-Ala-Pro-Pro-Ala-Pro-Pro-Gln-phosphorylated Ser-Pro-Phe as set forth in SEQ ID NO:11. This exemplary peptide is also denoted herein as L803F.

As used herein the phrase "hydrophobic moiety" refers to any substance that is characterized by hydrophobicity, namely, its solubility in water is much lower than its solubility in hydrophobic organic solvents, as defined herein.

In some embodiments, any hydrophobic moiety that is structurally suitable for interacting with a hydrophobic patch within a GSK-3 dimer, can be attached to the polypeptide described above.

The hydrophobic patch has been previously described by Dajani et al. (2001, supra). The crystallization data of Dajani et al. showed that GSK-3 is crystallized as a dimer, suggesting that this dimerization has biological relevance. The catalytic region (residues 216-220) of one monomer (a) appears to interact with the N-terminus of an α-helix (residues 262-273) of the other monomer (b). This interaction of the two monomers (a) and (b) forms a hydrophobic patch in monomer (b).

Alternatively, or in addition, the hydrophobic moiety is selected such that it enhances cell permeability of the peptide. Enhanced cell permeability can be determined by any method known in the art, for example, by determining a cellular uptake in in vitro studies.

Representative examples of hydrophobic substances from which the hydrophobic moiety of the present invention can be derived include, without limitation, substituted and unsubstituted, saturated and unsaturated hydrocarbons, where the hydrocarbon can be an aliphatic, an alicyclic or an aromatic compound and preferably includes at least 4 carbon atoms, more preferably at least 8 carbon atoms, more preferably at least 10 carbon atoms. In some embodiments, the hydrocarbon bears a functional group which enables its attachment to an amino acid residue. Representative examples of such a functional group include, without limitation, a free carboxylic acid (C(=O)OH), a free amino group ($NH_2$), an ester group (C(=O)OR, where R is alkyl, cycloalkyl or aryl), an acyl halide group (C(=O)A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(=O)—OR', where each of R' and R" is independently hydrogen, alkyl, cycloalkyl or aryl), a free N-carbamic group (OC(=O)—NR'—, where R' is as defined above), a thionyl group (S(=O)$_2$A, where A is halide as defined above) and the like.

In some embodiments, the hydrophobic moiety comprises one or more fatty acid(s).

Representative examples of fatty acids that are usable in the context of the present invention include, without limitation, saturated or unsaturated fatty acids that have more than 10 carbon atoms, preferably between 12 and 24 carbon atoms, such as, but not limited to, myristic acid, lauric acid, palmitic acid, stearic acid, oleic acid, linoleic acid, linolenic acid, arachidonic etc., with myristic acid being presently the most preferred.

The hydrophobic moiety according to some embodiments of the present invention can be a fatty acid, or derived from any other hydrophobic substance as described above, per se, such that the fatty acid, or any other hydrophobic substance, is covalently attached directly to an amino acid residue of the peptide (via, for example, en ester bond or an amide bond). Alternatively, the hydrophobic moiety can be an amino acid residue that is modified to include a fatty acid, or any other hydrophobic substance as described hereinabove, such that this modified amino acid residue is attached to the peptide via a peptide bond or a substituted peptide bond, as is described herein. Further alternatively, the hydrophobic moiety can be a short peptide in which one or more amino acid residues are modified to include a fatty acid or any other hydrophobic substance as described herein. Such a peptide preferably includes between 2 and 15 amino acid residues and is attached to the peptide via a peptide bond or a substituted peptide bond, as is described herein.

As an alternative to, or in combination with the hydrophobic moiety described above, the hydrophobic moiety, according to the present invention, can comprise a hydrophobic peptide sequence. The hydrophobic peptide sequence, according to the present invention, preferably includes between 2 and 15 amino acid residues, more preferably between 2 and 10 amino acid residues, more preferably between 2 and 5 amino acid residues, in which at least five consecutive amino acid residues are hydrophobic amino acid residues.

Alternatively, the hydrophobic amino acid residue can include any other amino acid residue, which has been modified by incorporation of a hydrophobic moiety thereto.

The hydrophobic moiety or moieties of the present invention are preferably attached to one or more termini of the peptide, namely the N-terminus and/or the C-terminus of the polypeptide. In some embodiments, the hydrophobic moiety is attached, directly or indirectly, as described herein, to the N-terminus of the polypeptide.

An exemplary peptide has the following amino acid sequence:

Myristic-Gly-Lys-Glu-Ala-Pro-Pro-Ala-Pro-Pro-Gln-phosphorylated Ser-Pro-Phe as set forth in SEQ ID NO:12. This exemplary peptide is also denoted herein as L803F-mts.

Additional exemplary peptides are those represented by the general amino acid sequence I, as described herein, which have a hydrophobic moiety attached thereto, as described herein. Any combination of such peptides and a hydrophobic moiety as described herein (e.g., a fatty acid as described herein and/or an amino acid substituted by a fatty acid as described herein and/or a hydrophobic amino acid sequence as described herein) is contemplated.

Further according to embodiments of the present invention, there is provided a process of preparing the peptides described herein.

In one embodiment, the peptide of the present invention is prepared by a chemical synthesis, using well known chemical procedures, such as solution or solid-phase peptide synthesis, or semi-synthesis in solution. The peptide can be chemically synthesized, for example, by the solid phase peptide synthesis of Merrifield et al (1964). Alternatively, a peptide can be synthesized using standard solution methods (see, for example, Bodanszky, 1984). Newly synthesized peptides can be purified, for example, by high performance liquid chromatography (HPLC), and can be characterized using, for example, mass spectrometry or amino acid sequence analysis.

Alternatively, the peptides of the invention can be provided recombinantly. Systems for cloning and expressing the peptide include various microorganisms and cells that are well known in recombinant technology. These include, for example, various strains of *E. coli, Bacillus, Streptomyces*, and *Saccharomyces*, as well as mammalian, yeast and insect cells. The peptide can be produced as a peptide or fusion protein (e.g., tagged peptide). Suitable vectors for producing the peptide are known and available from private and public laboratories and depositories and from commercial vendors. See Sambrook et al, (1989). Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses that can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething et al, 1981).

Once the peptide is provided, a hydrophobic moiety or moieties can be conjugated thereto, if desired, by commonly used techniques. For example, in cases where the hydrophobic moiety is a fatty acid, techniques for adding a fatty acid (e.g., myristic acid) to an amino acid residue within the peptide sequence are used. Alternatively, an amino acid residue is modified to include a hydrophobic moiety such as fatty acid and is thereafter attached to the peptide by known chemical procedures, as is described hereinabove.

In cases where the hydrophobic moiety comprises a hydrophobic peptide sequence, the hydrophobic peptide can be prepared using the methods described hereinabove and thereafter be conjugated to the polypeptide. Alternatively, the conjugate can be prepared recombinantly, using systems, as described hereinabove, for cloning and expressing a fused polypeptide that comprises the peptide as described herein and such a hydrophobic peptide sequence.

As is demonstrated in the Examples section that follows, an exemplary peptide according to some embodiments of the present invention exhibits high inhibitory effect toward GSK-3.

As is discussed hereinabove, the peptides disclosed herein are characterized by specificity towards GSK-3, a specificity which is derived from the unique recognition motif of GSK-3, which, unlike other kinases, includes a phosphorylated serine or threonine residue, and the fact that the sequence of the peptide portion thereof is based on this recognition motif.

The additional manipulation made to the GSK-3 recognition motif while designing the peptides disclosed herein render these peptides efficient substrate competitive inhibitors of GSK-3, and thus more specific as compared with other protein kinase inhibitors that are typically ATP competitive compounds and thus non-specific.

Thus, the high inhibitory activity of the peptides disclosed herein is derived from both, the replacement of the phosphorylated residue at the Z position by a non-phosphorylated residue, which renders the enzyme inactive in phosphorylation, and the incorporation of an e.g., aromatic amino acid residue at the indicated position (upstream a phsophorylated serine or threonine), which provides for enhanced interaction with a subunit of the enzyme's catalytic binding site, as discussed herein.

Hence, according to another aspect of some embodiments of the present invention, there is provided a method of inhibiting an activity of GSK-3, which is effected by contacting cells expressing GSK-3 with an effective amount of any of the peptides described herein.

As used herein, the term "effective amount" is the amount determined by such considerations as are known in the art, which is sufficient to reduce the activity of GSK-3 by at least 5%, at least 10%, at least 20%, at least 50% and even at least 80%, 90% or by 100%. Typical assays for measuring kinase activity can be used for determining the inhibitory activity of the peptides as described herein.

As is demonstrated in the Examples section that follows, a representative example of a peptide according to some embodiments of the present invention strongly inhibits GSK-3, with an $IC_{50}$ value of about 150 μM, as measured by in vitro kinase assay.

Hence, the effective amount of a peptide as described herein can range from about 0.1 micromolar to about 200 micromolar, or from about 1 micromolar and about 200 micromolar, or from about 10 micromolar to about 200 micromolar, or from about 100 micromolar to about 200 micromolar, including any intermediate value between the indicated ranges.

The method according to this aspect of the present invention can be effected by contacting the cells with the described peptides in vitro, ex vivo and in vivo.

Cells expressing GSK-3 can be derived from any biological sample, including, but not limited to, cell cultures or extracts thereof, enzyme preparations suitable for in vitro assays, biopsied material obtained from a mammal or extracts thereof, and samples of blood, saliva, urine, feces, semen, tears, spinal fluid, and any other fluids or extracts thereof.

In some embodiments, the method according to these embodiments, utilizes the peptides as described herein as active agents in biological assays, and in particular, as GSK-3 (substrate competitive) inhibitors in such assays.

As the peptides described herein do not include the required phosphorylated residue (at the Z position), GSK-3, while being bound thereto, is rendered inactive in phosphorylation reactions. Thus, the method according to these embodiments of the present invention preferably pertains to inhibition of the phosphorylation and/or autophosphorylation activity of GSK-3. In some embodiments, the activity is phosphorylation activity.

The method according to these embodiments of the present invention can be further effected by contacting the cells with an additional active ingredient that is capable of altering an activity of GSK-3, as is detailed hereinbelow.

The inhibition of GSK-3 activity is a way to increase insulin activity in vivo. High activity of GSK-3 impairs insulin action in intact cells. This impairment results from the phosphorylation of insulin receptor substrate-1 (IRS-1) serine residues by GSK-3. Studies performed in patients with type II diabetes (non-insulin dependent diabetes mellitus, NIDDM) show that glycogen synthase activity is markedly decreased in these patients, and that decreased activation of protein kinase B (PKB), an upstream regulator of GSK-3, by insulin is also detected. Mice susceptible to high fat diet-induced diabetes and obesity have significantly increased GSK-3 activity in epididymal fat tissue. Increased GSK-3 activity expressed in cells resulted in suppression of glycogen synthase activity.

Inhibition of GSK-3 activity therefore provides a useful method for increasing insulin activity in insulin-dependent conditions. For example, treatment with the peptides as described herein can result in improved glucose uptake and/or glucose tolerance.

Thus, according to another aspect of the present invention there is provided a method of potentiating insulin signaling, which is effected by contacting insulin responsive cells with an effective amount, as is defined hereinabove, of the peptide as described herein.

Contacting can be effected in vitro, as described herein, for example, by contacting a biological sample as described herein with one or more of the peptides described herein, or ex vivo, or in vivo, by administering a peptide as described herein to a patient in need thereof.

As used herein, the phrase "potentiating insulin signaling" includes an increase in the phosphorylation of insulin receptor downstream components and an increase in the rate of glucose uptake as compared with glucose uptake in untreated subjects or cells.

Potentiation of insulin signaling, in vivo, resulting from administration of the peptides as described herein, can be monitored as a clinical endpoint. In principle, the easiest way to look at insulin potentiation in a patient is to perform the glucose tolerance test. After fasting, glucose is given to a patient and the rate of the disappearance of glucose from blood circulation (namely glucose uptake by cells) is measured by assays well known in the art. Slow rate (as compared to healthy subject) of glucose clearance will indicate insulin resistance. The administration of a GSK-3 inhibitor such as the peptides described herein to an insulin-resistant patient increases the rate of glucose uptake as compared with a non-treated patient. The peptide may be administered to the patient for a longer period of time, and the levels of insulin, glucose, and leptin in blood circulation (which are usually high) may be determined. Decrease in glucose levels will indicate that the peptide potentiated insulin action. A decrease in insulin and leptin levels alone may not necessarily indicate potentiation of insulin action, but rather will indicate improvement of the disease condition by other mechanisms.

By inhibiting GSK-3 activity and/or potentiating insulin signaling, the peptides described herein may be effectively utilized for treating any biological condition that is associated with GSK-3.

Hence, according to another aspect of some embodiments of the present invention, there is provided a method of treating a biological condition associated with GSK-3 activity. The method, according to this aspect of the present invention, is effected by administering to a subject in need thereof a therapeutically effective amount of the peptide as described herein.

The phrase "biological condition associated with GSK-3 activity" as used herein includes any biological or medical condition or disorder in which effective GSK-3 activity is identified, whether at normal or abnormal levels. The condition or disorder may be caused by the GSK-3 activity or may simply be characterized by GSK-3 activity. That the condition is associated with GSK-3 activity means that some aspects of the condition can be traced to the GSK-3 activity. Such a biological condition can also be regarded as a biological or medical condition mediated by GSK-3.

Herein, the term "treating" includes abrogating, substantially inhibiting, slowing or reversing the progression of a condition or disorder, substantially ameliorating clinical symptoms of a condition or disorder or substantially preventing the appearance of clinical symptoms of a condition or disorder. These effects may be manifested, for non-limiting examples, by a decrease in the rate of glucose uptake with respect to type II diabetes or by halting neuronal cell death with respect to neurodegenerative disorders, as is detailed hereinbelow.

The term "administering" as used herein describes a method for bringing a peptide as described herein and cells affected by the condition or disorder together in such a manner that the peptide can affect the GSK-3 activity in these cells. The peptides described herein can be administered via any route that is medically acceptable. The route of administration can depend on the disease, condition, organ or injury being treated. Possible administration routes include injections, by parenteral routes, such as intravascular, intravenous, intra-arterial, subcutaneous, intramuscular, intratumor, intraperitoneal, intraventricular, intraepidural, intracerebroventricular, intranasal or others, as well as via oral, nasal, ophthalmic, rectal or topical routes of administration, or by inhalation. Sustained release administration is also encompassed herein, by means such as, for example, depot injections or erodible implants, or by sustained release oral formulations (e.g., solid oral formulations). Administration can also be intra-articularly, intrarectally, intraperitoneally, intramuscularly, subcutaneously, or by aerosol inhalant. Where treatment is systemic, the peptide can be administered orally, nasally or parenterally, such as intravenously, intramuscularly, subcutaneously, intraorbitally, intracapsularly, intraperitoneally or intracisternally, as long as provided in a composition suitable for effecting the introduction of the peptide into target cells, as is detailed hereinbelow.

In some embodiments, administration is effected nasally, namely via a nasal route of administration. A nasal administration can be effected either by intranasal injection or by means of a spray or liquid formulation that is administered nasally.

The phrase "therapeutically effective amount", as used herein, describes an amount administered to an individual, which is sufficient to abrogate, substantially inhibit, slow or reverse the progression of a condition associated with GSK-3 activity, to substantially ameliorate clinical symptoms of a such a condition or substantially prevent the appearance of clinical symptoms of such a condition. The GSK-3 activity can be a GSK-3 kinase activity. The inhibitory amount may be determined directly by measuring the inhibition of a GSK-3 activity, or, for example, where the desired effect is an effect on an activity downstream of GSK-3 activity in a pathway that includes GSK-3, the inhibition may be measured by measuring a downstream effect. Thus, for example where inhibition of GSK-3 results in the arrest of phosphorylation of glycogen synthase, the effects of the peptide may include effects on an insulin-dependent or insulin-related pathway, and the peptide may be administered to the point where glucose uptake is increased to optimal levels. Also, where the inhibition of GSK-3 results in the absence of phosphorylation of a protein that is required for further biological activity, for example, the tau protein, then the peptide may be administered until polymerization of phosphorylated tau protein is substantially arrested. Level of hippocampous β-catenin are also indicative for an effect on GSK-3 activity. Therefore, the inhibition of GSK-3 activity will depend in part on the nature of the inhibited pathway or process that involves GSK-3 activity, and on the effects that inhibition of GSK-3 activity has in a given biological context.

The amount of the peptide that will constitute an inhibitory amount will vary depending on such parameters as the peptide and its potency, the half-life of the peptide in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the peptide or that will have an effect on GSK-3 activity, or a pathway mediated by GSK-3 activity.

Although it is expected that the inhibitory amount will fall in a relatively broad range that can be determined through routine trials, an exemplary therapeutically effective amount according to the present invention is selected so as to achieve, at the treated site, an amount of the peptide that ranges between about 10 nmol and about 1000 nmol, or between about 10 nmol and about 500 nmol, or between about 100 nmol and about 400 nmol.

As is discussed in detail hereinabove, GSK-3 is involved in various biological pathways and hence, the method according to this aspect of the present invention can be used in the treatment of a variety of biological conditions, as is detailed hereinunder.

GSK-3 is involved in the insulin signaling pathway and therefore, in one example, the method according this aspect of the present invention can be used to treat any insulin-dependent condition.

By "insulin-dependent condition" it is meant any condition that is mediated by insulin and which is manifested or caused by reduced level of insulin or impaired insulin potentiation pathway. Exemplary such conditions include, but are not limited to, conditions that involve glucose intolerance and impaired glucose uptake, such as diabetes, including, for example, insulin-dependent diabetes and juvenile diabetes.

As GSK-3 inhibitors are known to inhibit differentiation of pre-adipocytes into adipocytes, in another example, the method of this aspect of the present invention can be used to treat obesity.

In yet another example, the method according to this aspect of the present invention can be used to treat diabetes including non-insulin dependent diabetes mellitus.

Diabetes mellitus is a heterogeneous primary disorder of carbohydrate metabolism with multiple etiologic factors that generally involve insulin deficiency or insulin resistance or both. Type I, juvenile onset, insulin-dependent diabetes mellitus, is present in patients with little or no endogenous insulin secretory capacity. These patients develop extreme hyperglycemia and are entirely dependent on exogenous insulin therapy for immediate survival. Type II, or adult onset, or non-insulin-dependent diabetes mellitus, occurs in patients who retain some endogenous insulin secretory capacity, but the great majority of them are both insulin deficient and insulin resistant. Approximately 95% of all diabetic patients in the United States have non-insulin dependent, Type II diabetes mellitus (NIDDM), and, therefore, this is the form of diabetes that accounts for the great majority of medical problems. Insulin resistance is an underlying characteristic feature of NIDDM and this metabolic defect leads to the diabetic syndrome. Insulin resistance can be due to insufficient insulin receptor expression, reduced insulin-binding affinity, or any abnormality at any step along the insulin signaling pathway (see U.S. Pat. No. 5,861,266).

The peptides described herein can be used to treat type II diabetes in a patient with type II diabetes as follows: a therapeutically effective amount of the peptide is administered to the patient, and clinical markers, e.g., blood sugar level, are monitored. The peptide can further be used to prevent type II diabetes in a subject as follows: a prophylactically effective amount of the peptide is administered to the patient, and a clinical marker, for example IRS-1 phosphorylation, is monitored.

Treatment of diabetes is determined by standard medical methods. A goal of diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycated hemoglobin level ($HbA_{1c}$; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with diabetic eye disease, kidney disease, or nerve disease.

Hence, in one particular embodiment of the method according to this aspect of the present invention, there is provided a method of treating non-insulin dependent diabetes mellitus: a patient is diagnosed in the early stages of non-insulin dependent diabetes mellitus. A peptide as described herein is formulated in an enteric capsule. The patient is directed to take one tablet after each meal for the purpose of stimulating the insulin signaling pathway, and thereby controlling glucose metabolism to levels that obviate the need for administration of exogenous insulin In another example, the method according to these embodiments of the present invention can be used to treat affective disorders such as unipolar disorders (e.g., depression) and bipolar disorders (e.g., manic depression). As is demonstrated herein, the effect of the peptides as described herein was exemplified on up-regulation of β-catenin levels, thus indicating, a role of these GSK-3 inhibitors in the treatment of affective disorders.

As GSK-3 is also considered to be an important player in the pathogenesis of neurodegenerative disorders and diseases, the method according to this aspect of the present invention can be further used to treat a variety of such disorders and diseases.

In one example, since inhibition of GSK-3 results in halting neuronal cell death, the method according to these embodiments of the present invention can be used to treat a neurodegenerative disorder that results from an event that cause neuronal cell death. Such an event can be, for example, cerebral ischemia, stroke, traumatic brain injury or bacterial infection.

In another example, since GSK-3 activity is implicated in various central nervous system disorders and neurodegenerative diseases, the method according to these embodiments can be used to treat various chronic neurodegenerative diseases such as, but not limited to, Alzheimer's disease, Huntington's disease, Parkinson's disease, AIDS associated dementia, amyotrophic lateral sclerosis (AML) and multiple sclerosis.

As is discussed hereinabove, GSK-3 activity has particularly been implicated in the pathogenesis of Alzheimer's disease. Hence, in one representative embodiment of the method described herein, there is provided a method of treating a patient with Alzheimer's disease: A patient diagnosed with Alzheimer's disease is administered with a peptide as described herein, which inhibits GSK-3-mediated tau hyperphosphorylation, prepared in a formulation that crosses the blood brain barrier (BBB). The patient is monitored for tau phosphorylated polymers by periodic analysis of proteins isolated from the patient's brain cells for the presence of phosphorylated forms of tau on an SDS-PAGE gel known to characterize the presence of and progression of the disease. The dosage of the peptide is adjusted as necessary to reduce the presence of the phosphorylated forms of tau protein.

GSK-3 has also been implicated with respect to psychotic disorders such as schizophrenia, and therefore the method according to these embodiments of the present invention can be further used to treat psychotic diseases or disorders, such as schizophrenia.

GSK-3 has also been implicated with respect to affective disorders. Therefore, in another example, the method according to this aspect of the present invention can be used to treat affective disorders such as unipolar disorders (e.g., depression) and bipolar disorders (e.g., manic depression).

It should be noted that the peptides described herein are particularly advantageous in the treatment of psychotic, affective and neurodegenerative diseases or disorders since, apart from exerting enhanced inhibition activity of GSK-3, it is postulated that the inclusion of multiple hydrophobic amino acid residues within the peptides further provides for enhanced lipophilicity of the peptides and, as a result, for enhanced permeability through the blood brain barrier (BBB). This enhanced permeability may allow a systemic, rather than local, administration of the peptides, such that the need to administer the inhibitors intracerebroventricularly (icv) is avoided.

GSK-3 has also been implicated with respect to cardiovascular conditions, and therefore, the peptides described herein can be further used to treat cardiovascular diseases or disorders.

Cardiovascular diseases and disorders include, but are not limited to, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, and anti-helper T lymphocyte autoimmunity.

GSK-3 has also been implicated with respect to conditions (e.g., infections) associated with pathogenic parasites (e.g., malaria and trypanosomiasis), and therefore, the peptides described herein can be further used to treat a condition (e.g., infection) that is associated with a presence of a pathogenic parasite in a subject. Exemplary parasites include *Acanthamoeba, Anisakis, Ascaris lumbricoides*, Botfly, *Balantidium coli*, Bedbug, Cestoda (tapeworm), Chiggers, *Cochliomyia hominivorax, Entamoeba histolytica, Fasciola hepatica, Giardia lamblia*, Hookworm, *Leishmania, Linguatula serrata*, Liver fluke, *Loa boa, Paragonimus*—lung fluke, Pinworm, *Schistosoma, Strongyloides stercoralis*, Mites, Tapeworm, *Toxoplasma gondii, Trypanosoma*, Whipworm, *Wuchereria bancrofti* and *Plasmodium falciparum* and related malaria-causing protozoan parasites.

Exemplary conditions caused by pathogenic parasites include, but are not limited to, Acanthamoeba keratitis, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis (caused by the Guinea worm), Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis (cause of Cysticercosis), Toxocariasis, Toxoplasmosis, Trichinosis and Trichuriasis.

GSK-3 has also been suggested to be involved in stem cell maintenance and/or differentiation. Accordingly, the peptides described herein can be further utilized in the treatment of conditions in which transplantation of stem cells is used as part of the treatment. Such conditions include, for example, cancer and damaged tissues (treatable by tissue regeneration).

In some embodiments, the peptides described herein can be utilized for maintaining and/or differentiating stem cells. Thus, in some embodiments, there is provided a method of maintaining and/or differentiating stem cells, which is effected by contacting a peptide as described herein with stem cells. In some embodiments, the contacting is effected ex-vivo. In some embodiments, the contacting is effected in the presence of a physiological medium, as acceptable for stem cells preparations. In some embodiments, the contacting is effected by placing stem cells in a suitable medium which further comprises a peptide as described herein.

The method according to this aspect of the present invention can be further effected by co-administering to the subject one or more additional active ingredient(s) which is capable of altering an activity of GSK-3.

As used herein, "co-administering" describes administration of a peptide as described herein in combination with the additional active ingredient(s) (also referred to herein as active or therapeutic agent). The additional active agent can be any therapeutic agent useful for treatment of the patient's condition. The co-administration may be simultaneous, for example, by administering a mixture of the peptide and the additional therapeutic agent, or may be accomplished by administration of the peptide and the active agent separately, such as within a short time period. Co-administration also includes successive administration of the peptide and one or more of another therapeutic agent. The additional therapeutic agent or agents may be administered before or after the peptide. Dosage treatment may be a single dose schedule or a multiple dose schedule.

An example of an additional active agent is insulin.

Preferably, the additional active agent is capable of inhibiting an activity of GSK-3, such that the additional active agent can be any GSK-3 inhibitor other than the peptides described herein, and thus can be, as non-limiting examples, lithium, valproic acid and other peptides or small molecules that are shown to inhibit GSK-3 activity as described herein.

Alternatively, the additional active agent can be an agent that is capable of downregulating an expression of GSK-3.

An agent that downregulates GSK-3 expression refers to any agent which affects GSK-3 synthesis (decelerates) or degradation (accelerates) either at the level of the mRNA or at the level of the protein. For example, a small interfering polynucleotide molecule which is designed to downregulate the expression of GSK-3 can be used as an additional active agent according to some embodiments of the present invention.

An example for a small interfering polynucleotide molecule which can down-regulate the expression of GSK-3 is a small interfering RNA or siRNA, such as, for example, the morpholino antisense oligonucleotides described by in Munshi et al. (Munshi C B, Graeff R, Lee H C, *J Biol Chem* 2002 Dec. 20; 277(51):49453-8), which includes duplex oligonucleotides which direct sequence specific degradation of mRNA through the previously described mechanism of RNA interference (RNAi) (Hutvagner and Zamore (2002) Curr. Opin. Genetics and Development 12:225-232).

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

Preferably, the specific small interfering duplex oligonucleotide of the present invention is an oligoribonucleotide composed mainly of ribonucleic acids.

Instructions for generation of duplex oligonucleotides capable of mediating RNA interference are provided in wwwdotambiondotcom.

Hence, the small interfering polynucleotide molecule according to some embodiments of the present invention can be an RNAi molecule (RNA interference molecule).

Alternatively, a small interfering polynucleotide molecule can be an oligonucleotide such as a GSK-3-specific antisense molecule or a ribozyme molecule, further described hereinunder.

Antisense molecules are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA: DNA or RNA:RNA hybrids. An example for such includes RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

The antisense molecules of the present invention may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366, 878; 5,403,711; 5,491,133; 5,565,350; 5,623,065; 5,652, 355; 5,652,356; and 5,700,922, each of which is herein fully incorporated by reference.

Rybozyme molecules are being increasingly used for the sequence-specific inhibition of gene expression by the cleavage of mRNAs. Several rybozyme sequences can be fused to the oligonucleotides of the present invention. These sequences include but are not limited ANGIOZYME specifically inhibiting formation of the VEGF-R (Vascular Endothelial Growth Factor receptor), a key component in the angiogenesis pathway, and HEPTAZYME, a rybozyme designed to selectively destroy Hepatitis C Virus (HCV) RNA, (Rybozyme Pharmaceuticals, Incorporated—WEB home page).

Further alternatively, a small interfering polynucleotide molecule, according to the present invention can be a DNAzyme.

DNAzymes are single-stranded catalytic nucleic acid molecules. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M Curr Opin Mol Ther 2002; 4:119-21).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther wwwdotasgtdotorg). In another application, DNAzymes complementary to bcr-ab1 oncogenes were successful in inhibiting the oncogenes expression in leukemia cells, and lessening relapse rates in autologous bone marrow transplant in cases of CML and ALL.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Further according to embodiments of the present invention there is provided a use of the peptides as described herein in the manufacture of a medicament for treating a biological condition associated with GSK-3 activity, as described herein.

Further according to embodiments of the present invention there is provided a peptide as described herein, which is identified for use in the treatment of a biological condition associated with GSK-3 activity, as described herein.

In any of the methods and uses described herein, the peptides described herein can be utilized in combination with one or more additional active ingredient(s) or agent(s) which is capable of altering an activity of GSK-3, as described herein.

In any of the methods and uses described herein the peptide described herein can be utilized either per se, or, preferably, the peptide forms a part of a pharmaceutical composition, which may further comprise a pharmaceutically acceptable carrier.

As used herein a "pharmaceutical composition" refers to a preparation of one or more of the peptides described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject.

The term "active ingredient", which is also referred to herein interchangeably as "active agent" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, nasally, by inhalation, or parenterally, for example by intravenous drip or intraperitoneal, subcutaneous, intramuscular or intravenous injection, or topically (including ophtalmically, vaginally, rectally and intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described herein is packaged in a packaging material and identified in print, in or on the packaging material, for use in the treatment of a medical condition associated with GSK-3 activity, as described herein.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In some embodiments, the pharmaceutical composition is identified for use in combination with an additional active agent, as described herein.

In some embodiments, the pharmaceutical composition further comprises an additional active agent as described herein, being co-formulated with the peptide as described herein.

General:

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "polypeptide" and "peptide" encompass an amino acid sequence of any length including full-length proteins or portions thereof, wherein the amino acid residues are linked by covalent peptide bonds. Generally, an amino acid sequence of 50 amino acids and more are referred to herein as "polypeptide" or "protein", and an amino acid sequence of less than 50 amino acids is referred to herein as "peptide".

The term "peptide" as used herein encompasses also peptoids and semipeptoids which are peptide analogs, which may have, for example, modifications rendering the peptides more stable while in a body or more capable of penetrating into cells. Such modifications include, but are not limited to N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, the peptides described herein are chemically synthesized peptides.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time.

As used herein, the phrase "amino acid residue", which is also referred to herein, interchangeably, as "amino acid", describes an amino acid unit within a polypeptide chain. The amino acid residues within the peptides described herein can be either natural or modified amino acid residues, as these phrases are defined hereinafter.

As used herein, the phrase "natural amino acid residue" describes an amino acid residue, as this term is defined hereinabove, which includes one of the twenty amino acids found in nature.

As used herein, the phrase "modified amino acid residue" describes an amino acid residue, as this term is defined hereinabove, which includes a natural amino acid that was subjected to a modification at its side chain. Such modifications are well known in the art and include, for example, incorporation of a functionality group such as, but not limited to, a hydroxy group, an amino group, a carboxy group and a phosphate group within the side chain. This phrase therefore includes, unless otherwise specifically indicated, chemically modified amino acids, including amino acid analogs (such as penicillamine, 3-mercapto-D-valine), naturally-occurring non-proteogenic amino acids (such as norleucine), and chemically-synthesized compounds that have properties known in the art to be characteristic of an amino acid. The term "proteogenic" indicates that the amino acid can be incorporated into a protein in a cell through well-known metabolic pathways.

Accordingly, as used herein, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids which are linked via a peptide bond or a peptide bond analog to at least one addition amino acid as this term is defined herein.

The peptides of the present embodiments are preferably utilized in a linear form, although it will be appreciated that in cases where cyclization does not severely interfere with peptide characteristics, cyclic forms of the peptide can also be utilized).

Cyclic peptides can either be synthesized in a cyclic form or configured so as to assume a cyclic form under desired conditions (e.g., physiological conditions).

The peptides of the present embodiments are preferably peptidomimetics, as this term is define hereinabove, which mimic the structural features of the critical amino acid motif $ZX_1X_2X_3S(p)$, as is further detailed hereinabove.

Protein phosphorylation plays a crucial part in the biochemical control of cellular activity. Phosphorylation usually means formation of a phosphate ester bond between a phosphate ($PO_4$) group and an amino acid containing a hydroxyl (OH) group (tyrosine, serine and threonine). Many phosphorylation sites in proteins act as recognition elements for binding to other proteins, and those binding events activate or deactivate signaling and other pathways. Protein phosphorylation thus acts as a switch to turn biochemical signaling on and off.

Phosphopeptide mimetics are a subclass of peptidomimetics that contain analogs of phosphorylated tyrosine, serine and threonine. Phosphate esters may be hydrolyzed by various enzymes, thus turning off a phosphorylation signal. Phosphopeptide mimetics, however, usually contain non-hydrolyzable analogs to prevent inactivation (Burke et al, 1994a; Burke et al, 1996a; Chen et al, 1995; Wiemann et al, 2000; Shapiro et al, 1997; Otaka et al, 1995; Otaka et al, 2000). General examples of phosphopeptide mimetics in the art include SH2 domain analogs (Burke et al, 1994a; Fu et al, 1998; Gao et al, 2000; Mikol et al, 1995; Ye et al, 1995), transcription factor NF-(kappa)B analog (McKinsey et al, 1997), P53 analog (Higashimoto et al, 2000) and protein-tyrosine phosphatase inhibitors (Burke et al, 1994b; Burke et al, 1996b; Groves et al, 1998; Kole et al, 1995; Kole et al, 1997; Roller et al, 1998).

Commercially available software packages can be used to design small peptides and/or peptidomimetics containing, phosphoserine or phosphothreonine analogs, preferably non-hydrolyzable analogs, as specific antagonists/inhibitors. Suitable commercially available software for analyzing crystal structure, designing and optimizing small peptides and peptidomimetics include, but are not limited to: Macromolecular X-ray Crystallography QUANTA Environment (Molecular Simulations, Inc.); TeXsan, BioteX, and SQUASH (Molecular Structure Corporation); and Crystallographica (Oxford Cryostsystems).

The peptides according to the present embodiments can further include salts and chemical derivatives of the peptides. As used herein, the phrase "chemical derivative" describes a peptide as described herein having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. Also included as chemical derivatives are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The chemical derivatization does not comprehend changes in functional groups which change one amino acid to another.

As is mentioned hereinabove, some useful modifications are designed to increase the stability of the peptide in solution and, therefore, serve to prolong the half-life of the peptide in solutions, particularly biological fluids, such as blood, plasma or serum, by blocking proteolytic activity in the blood. Hence, the peptides described herein can have a stabilizing group at one or both termini. Typical stabilizing groups include amido, acetyl, benzyl, phenyl, tosyl, alkoxycarbonyl, alkyl carbonyl, benzyloxycarbonyl and the like end group modifications. Additional modifications include using one or more "D" amino acids in place of "L" amino acid(s), cyclization of the peptide inhibitor, and amide rather than amino or carboxy termini to inhibit exopeptidase activity.

The peptides described herein may or may not be glycosylated. The peptides are not glycosylated, for example, when produced directly by peptide synthesis techniques or are produced in a prokaryotic cell transformed with a recombinant polynucleotide. Eukaryotically-produced peptide molecules are typically glycosylated. The term "hydrocarbon", as used herein, encompasses any moiety that is based on a linear and/or cyclic chain of carbons which are mainly substituted by hydrogens. A hydrocarbon can be a saturated or unsaturated moiety, and can optionally be substituted by one or more substituents, as described herein.

Any of the peptides described herein can be in a form of a pharmaceutically acceptable salt thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The present invention further encompasses prodrugs, solvates and hydrates of the peptides described herein.

As used herein, the term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be a peptide, as described herein, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the peptide) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Material and Methods

Materials:

Peptides were synthesized by Genemed Synthesis, Inc. (San Francisco, USA). The peptide substrates included p9CREB, ILSRRPS(p)YR (SEQ ID NO:14); pIRS-1, RREGGMSRPAS(p)VDG (SEQ ID NO:15); PGS-1, YRRAAVPPSPSLSRHSSPSQS(p)EDEEE (SEQ ID NO:16) as previously described [Ilouz et al. (2006) supra].

Peptide inhibitor L803 KEAPPAPPQS(p)P (SEQ ID NO:4) and the L803-mts (SEQ ID NO:5) in which myristic acid was attached to its N-terminal were described previously [Plotkin et al., 2003, supra].

Other L803 variants were synthesized as described herein.

Anti GSK-3β antibody was from Transduction Laboratory (Lexington, Ky., USA).

Anti-phospho-GSK3 ($Y^{216}$) was obtained from Upstate Biotechnology (Lake Placid, N.Y., USA).

Anti-phospho-CREB ($S^{129/133}$) was obtained from BioSource International, Inc. (Camarillo, Calif., USA).

CREB antibody was from Cell Signaling Technology (Beverly, Mass., USA).

Anti-phospho-IRS-1 ($S^{332}$) was generated as previously described [Liberman, Z. & Eldar-Finkelman, H. (2005) supra].

Radioactive materials were purchased from NEN PerkinElmer USA.

Plasmids and Mutants:

GSK-3β in the pCMV4 vector was used as the template for mutagenesis. Mutations were generated using QuickChange Site Directed Mutagenesis Kit (Stratagene, La Jolla, Calif., USA) according the manufacturer's protocols. Mutations included replacement of D90, K91, R92, F93, K94, to alanine, F93 to tyrosine, and a triple mutation at residues 91-93. All constructs were sequenced to confirm the presence of desired mutations. The sequences of mutagenic oligonucleotides are available from the inventors upon request.

N'IRS-1 (also termed PTB2) plasmid was previously described [Liberman, Z. & Eldar-Finkelman, H. (2005) supra].

CREB-GFP plasmid was purchased from Clontech (Mountain View, Calif., USA).

Cell Transfections and Protein Partial Purifications:

HEK-293 cells were grown in Dulbecco's Modified Eagle's Medium (DMEM), supplemented with 10% fetal calf serum (FCS), 2 mM glutamine, 100 units/ml penicillin, and 100 µg/ml streptomycin. HEK-293 cells were transiently transfected with indicated constructs, using calcium phosphate method as described [Ilouz et al. (2006) supra]. Cells were lysed in ice-cold buffer G (20 mM Tris-HCl, pH 7.5, 10 mM β-glycerophosphate, 10% glycerol, 1 mM EGTA, 1 mM EDTA, 50 mM NaF, 5 mM sodium pyrophosphate, 0.5 mM orthovanadate, 1 mM benzamidine, 10 µg/ml leupeptin, 5 µg/ml aprotinin, 1 µg/ml pepstatin, and 0.5% Triton X100). Cell extracts were centrifuged for 30 minutes at 15,000×g. Supernatants were collected, and equal amounts of proteins were boiled with SDS sample buffer and subjected to gel electrophoresis (7.5-12% polyacrylamide gel), transferred to nitrocellulose membranes, and immunoblotted with indicated antibodies. For partial purification, cells were lysed in buffer H (20 mM Tris, pH 7.3, 1 mM EGTA, 1 mM EDTA, 1 mM orthovanadate, 25 µg/ml leupeptin, 25 µg/ml aprotinin, and 25 µg/ml pepstatin A, 500 nM microcystine LR, and 0.25% Triton X100). The lysates were centrifuged at 15,000×g. The resulting supernatants were passed through DE-52 (Whatman, Maidstone, England) mini-columns that were equilibrated with buffer H. GSK-3β proteins were eluted with the same buffer containing 0.02 M NaCl. Equal amounts of proteins were used for in vitro kinase assays. In all experiments, GSK-3 mutants were expressed at levels at least 5-fold higher than levels of the endogenous GSK-3β as determined by western blot analysis.

In Vitro Kinase Assays:

The GSK-3β proteins (WT or mutants) were incubated with indicated substrate in a reaction mixture (50 mM Tris-HCl, pH 7.3, 10 mM magnesium acetate, and 0.01% β-mercaptoethanol) together with 100 µM $^{32}$P[γ-ATP] (0.5 µCi/assay) for 15 minutes. Reactions were stopped by spotting on p81 paper (Whatman) washed with phosphoric acid, and counted for radioactivity as previously described [Ilouz et al. (2006) supra]. In assays from cells overexpressing GSK-3 proteins, the activity of the endogenous GSK-3 that was determined in cells transfected with the pCMV4 vector was subtracted from the activity values obtained for WT and mutants.

Statistical Analysis:

Data were analyzed with Origin Professional 6.0 software using Student's t-test to compare GSK-3 activity of WT vs mutants or peptides-treatment vs. non treatment. Data were considered significant at p <0.05.

Molecular Dynamics:

Molecular dynamics (MD) simulations were performed with the program Gromacs [Van Der Spoel et al. (2005) *J. Comput. Chem.* 26, 1701-18] employing the united atoms gromos96 43a1 force field [van Gunsteren et al. (1996). Biomolecular Simulation: The Gromos 96 Manual and User Guide] modified to include phosphorylated residues [wwwdotgromacsdotorg/Downloads/User_contributions/ Force_fields].

The initial model of the solute (peptide or GSK-3β/ peptide complex) was immersed in a cube of water, neutralized and energy minimized. This was followed by a 1 ns MD simulation to equilibrate the water, keeping the non hydrogen atoms of the solute restrained. Next, additional 1 or 2 ns simulation was performed, of the peptide or GSK-3β/peptide complex in water. In the latter case the Cα atoms of GSK-3β were restrained and weak restrains were imposed on the distances between the phosphate oxygens of S10(p) in the peptide and the side chain nitrogen atoms of GSK-3β Arg 96, Arg 180, and Lys 205. Only the last 1 ns of each MD simulation was considered in the analysis of the trajectory (0.5 ns for the free peptides).

Rigid Body Docking:

Rigid body docking was performed with the geometric-electrostatic-hydrophobic version of MolFit [Berchanski et al. (2004) *Proteins* 351, 309-26]. The starting geometry of the GSK-3β/ATP complex was modeled as described before [Ilouz et al. (2006) supra]. Several starting geometries of the free peptide were used in docking, as representative conformers from clusters obtained in MD simulation of the free peptide in water. The comprehensive docking scans were followed by a new post-scan filtering procedure that incorporates statistical propensity measures and desolvation energy calculations [Kowalsman & Eisenstein (2009) *Proteins* 77, 297-318]. The filtered models were further screened requesting that S10(p) of the peptide makes contact with the positive cavity on the surface of GSK-313.

Anchoring Spots Mapping:

Anchoring spots mapping identifies preferred binding positions of amino acid side chains on the surface of a protein [Ben-Shimon and Eisenstein (2010) *J. Mol. Biol.* 402, 259-77]. This procedure was used here to detect amino acids that bind in the GSK-3β surface cavity bordered by loop 89-95 and the P-loop. Only side chains that bind with ΔG≤−4 Kcal/mol were considered.

Example 1

Defining a Substrate Binding Subsite in GSK-3

The Q89-N95 Segment:

The amino acid sequence segment delimited by Gln 89 and Asn 95 (as set forth is SEQ ID NO:2), two residues that were found to participate in GSK-3 substrate binding [Ilouz et al. 2006, supra], forms a loop (termed herein 89-95 loop) that together with the conserved P-loop, defines the borders of a surface cavity in GSK-3.

Figure 1A:
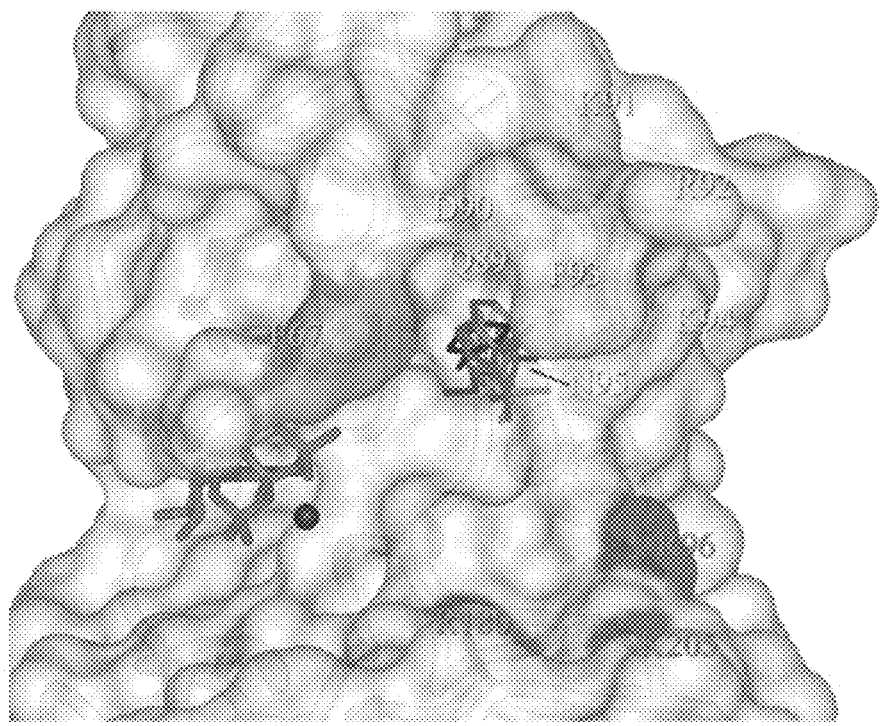

FIG. 1A presents features of the substrate binding site of GSK-3β. The structure of GSK-3β is based on the available crystal structures [Dajani et al. (2000) supra; Bertrand et al. (2003) supra], as described in Ilouz et al., 2006 [supra]. The surface of GSK-3β is shown in gray with the loop 89-95 shown in yellow and the P-loop residue Phe 67 emphasized in green. The positive ends of the residues that form the putative $PO_3^{-2}$ binding cavity are indicated in blue. The ATP molecule is colored by atom with the $Mg^{+2}$ ion in black. As can be seen in FIG. 1A, Q89, N95 and F93 form the bottom and a "wall" of a surface cavity located between the 89-95 loop and the P-loop.

Using the recently developed anchoring spots mapping procedure [Ben-Shimon & Eisenstein (2010). *J. Mol. Biol.* 402, 259-77], the present inventors have found that a variety of amino acid side chains can make favorable contacts within the surface cavity as shown in FIG. 1A. FIG. 1A thus further presents predicted positions of Arg (dark blue), Lys (blue), His (cyan), Gln (magenta), Ile (orange), Leu (green), Met (yellow), Phe (black), Trp (purple) and Tyr (red) bound to the cavity.

Figure 1B:
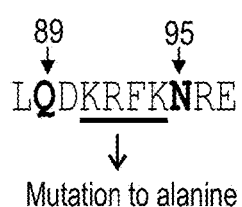
Figure 1C:
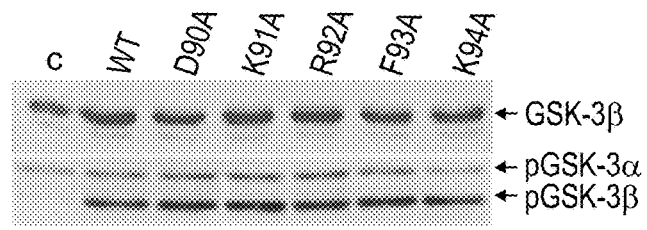

To further explore the role of the 89-95 loop in GSK-3β substrate binding, each of the amino acid residues within this segment was individually mutated to alanine (see, FIG. 1B). HEK-293 cells were transiently transfected with cDNA constructs expressing wild-type (WT) GSK-3β, and D90A, K91A, R92A, F93A, R94A mutant proteins (as set forth in SEQ ID NOS:6-10), as described in the Methods section hereinabove. Cell extracts were subjected to Western blot analysis using either anti-GSK-3β or antiphospho-GSK-3 (Tyr 216/Tyr 274 for α or β isoforms respectively) antibodies. Control (C) represents extracts from cells expressing the empty vector. All the mutants were expressed at levels considerably above that of the endogenous GSK-3β (FIG. 1C, upper panel). Like the wild-type (WT) GSK-3β, the mutants were phosphorylated at Tyr 216 (FIG. 1C, lower panel), indicating that their catalytic activity was not impaired by the mutation, as phosphorylation at Tyr 216 reflects an auto-phosphorylation process [as previously described in Cole et al. (2004) *Biochem. J.* 377, 249-55; and Eldar-Finkelman et al. (1996) *Proc. Natl. Acad. Sci. USA* 93, 10228-10233].

The GSK-3β mutants were partially purified by ion exchange chromatography, and their abilities to phosphorylate peptide substrates were tested in in vitro kinase assays. The substrates were: pIRS-1, p9CREB, and pGS-1, phosphorylated peptides derived from the insulin receptor substrate-1 (IRS-1), cAMP responsive element binding protein (CREB), and glycogen synthase, respectively.

The results are presented in Table 1, as the percentage of substrate phosphorylation (indicated peptides, pIRS-1, p9CREB and pGS-1) obtained with WT GSK-3β which was set to 100%, and are mean of 2-3 independent experiments each performed in duplicates ±SEM.

Figure 1D:
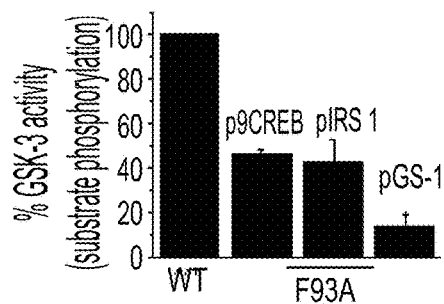

As shown in Table 1, three of the 5 mutants, R92A, F93A, K94A mutants, impaired the ability to phosphorylate the substrates; the mutation at Lys 91 enhanced substrate phosphorylation by about 20-30%; and, notably, that mutation at Phe 93 had the most deleterious effect for all substrates, reducing the kinase ability to phosphorylate them by more than 50% (see also FIG. 1D). A similar impact was previously observed with Q89A and N95A mutants [see, Ilouz et al., 2006, supra].

TABLE 1

| Mutant | Substrate phosphorylation (% of WTGSK-3β) | | |
|---|---|---|---|
| | pIRS-1 | p9CREB | pGS-1 |
| D90A (SEQ ID NO: 6) | 88 ± 15 | 92 ± 21 | 83 ± 2 |
| K91A (SEQ ID NO: 7) | 140 ± 18 | 161 ± 5 | 119 ± 5 |
| R92A (SEQ ID NO: 8) | 60 ± 3 | 49 ± 19 | 41 ± 14 |
| F93A (SEQ ID NO: 9) | 42 ± 13 | 46 ± 2 | 13 ± 7 |
| K94A (SEQ ID NO: 10) | 52 ± 19 | 71 ± 4 | 19 ± 14 |

FIG. 1D presents the phosphorylation of peptide substrates by F93A mutant. F93A was subjected to in vitro kinase assays with substrates pIRS-1, p9CREB, and PGS-1 as described in the Methods section hereinabove. The percentage of substrate phosphorylation obtained with WT-GSK-3β was defined as 100%, and results are means of 2-3 independent experiments each performed in duplicates ±SEM.

Hence, Phe93 adjoins Gln89 and Asn95 as an important substrate binding position within the 89-95 loop. As shown in FIG. 1A, Phe93 is located at the center of the 89-95 loop, it is highly exposed (81% solvent accessibility) and it faces the substrate binding subsite, facilitating contacts with variety of residues.

The role of Phe93 in substrate binding by employing a cellular system and protein substrates (i.e., not peptides) was further explored. To this end, the WT-GSK-3β and F93A mutant were expressed in HEK-293 cells together with GSK-3 substrates CREB or N'IRS-1 (the N-terminal region of IRS-1). Because GSK-3 requires pre-phosphorylation of its substrates, the cells were treated with forskolin to enhance CREB phosphorylation via activation of cAMP dependent kinase (PKA), or with phorbol ester (PMA) to enhance N'IRS-1 phosphorylation via activation of protein kinase C (PKC).

The phosphorylation of CREB at serine 129, and N'IRS-1 at serine 332 (both GSK-3 phosphorylation sites) was then examined.

Thus, HEK293 cells were co-transfected with WT-GSK-3β or F93A plasmids together with construct coding for CREB. Cells were treated with forskolin (10 μM, 1 hour), and cell extracts were subjected to Western blot analysis using anti-phospho CREB (Ser 129/133) antibody, as presented in FIG. 1E. Expression levels of CREB and GSK-3 proteins are indicated. The ratio of pCREB/CREB as calculated from densitometry analysis is shown in FIG. 1F. Results are means of three independent experiments ±SEM.

A similar assay was conducted using N'IRS-1 cDNA construct instead of CREB, and cells were treated with PMA (100 nM, 30 minutes). Anti-phospho IRS-1 (Ser332) antibody was used as indicated, and the results are presented in FIG. 1G. Expression levels of N'IRS-1 and GSK-3β are indicated. The ratio of pN'IRS-1/N'IRS-1 as calculated from densitometry analysis is shown in FIG. 1H. Results are means of three independent experiments ±SEM.

Figure 1E:
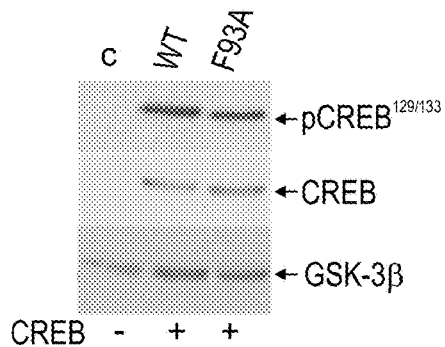
Figure 1F:
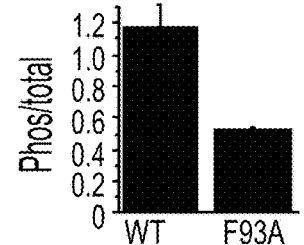
Figure 1G:
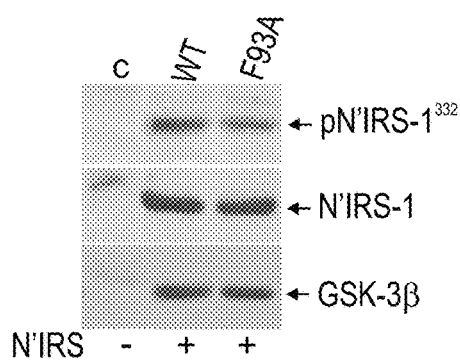
Figure 1H:
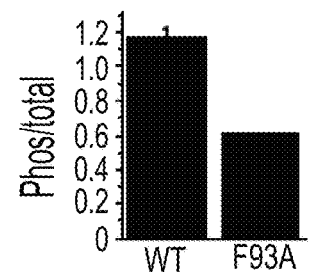

Unlike WT-GSK-3β, expression of F93A did not enhance the phosphorylation of these substrates as determined by specific anti-phospho-antibodies (see, FIGS. 1E-G). This substantiated the in vitro results showing that Phe93 interacts with GSK-3 substrates under cellular conditions.

The Role of Phe93 in the Inhibition of GSK-3 by the Substrate Competitive Inhibitor L803-mts:

Purified GSK-3β was subjected to in vitro kinase assays using pIRS-1, p9CREB, and pGS-1 substrate in the presence or absence of L803-mts (100 μM). As shown in FIG. 2A, L803-mts competes with various substrates, indicating that its binding mode with GSK-3 may share similar interactions to those of GSK-3 substrates.

The interaction of L803-mts with the 89-95 loop was thus examined. In vitro kinase assays were performed with WT-GSK-3β and the GSK-3β—mutants described hereinabove in the presence or absence of L803-mts. The results are presented in FIG. 2B and present the percentages of substrate phosphorylation obtained with the inhibitor versus phosphorylation without the inhibitor (defined as 100%), and are means of 2-3 independent experiments±SEM.

The results indicated that L803-mts did not inhibit F93A. This, in contrast to its ability to inhibit all other mutants including Q89A, N95A, R92A, K94A, F93Y and TM (91-93) (data not shown). Collectively, the results suggest that both L803-mts (and L803) and the substrates interact with Phe93, but, unlike the substrates, L803-mts does not interact with other residues within the 89-95 loop, including Gln89 and Asn95.

Example 2

Modeling GSK-3β Interactions with the Inhibitor

Predicting the binding modes of peptides is generally a difficult problem due to their inherent flexibility, which contributes to the high entropy of unbound peptides. This entropy barrier has to be overcome upon binding.

However, the exemplary inhibitor used in the conducted studies, L803 (see, SEQ ID NO:4), is proline rich, and is thus rather rigid. As shown in FIG. 3, Molecular dynamics (MD) simulation of L803 in water showed that the free L803 adopts a polyproline-like helix for part of its structures. The root mean square deviation (RMSD) for all non hydrogen atoms of the peptide in the last 0.3 ns of a 1 ns simulation is within 2.8 Å.

Rigid body docking of the modeled L803 to GSK-3β was executed with the geometric-electrostatic-hydrophobic version of MolFit followed by filtering based on statistical propensity measures and solvation energy estimates. This comprehensive search produced a single high ranking cluster of models, in which S10(p) of L803 docks into the phosphate binding cavity of GSK-3β. In these models L803 is positioned in a deep groove near the P-loop and it interacts with Phe93 and the hydrophobic surface patch formed by Val 214, Tyr 216 and Ile 217.

To further substantiate the rigid body docking model a 2 ns MD simulation of the GSK-3β/L803 complex in water was performed, starting with the peptide near the deep groove. The last 1 ns of the trajectory was clustered and FIG. 4 presents a representative snapshot from the largest cluster, reflecting the most abundant binding mode. The interaction with GSK-3β consists of a charged interaction between S10(p) of L803 and the positive phosphate binding pocket of GSK-3β and hydrophobic interactions between L803/P8 and in some instances also L803/P11 and GSK-313/F93 and between L803/P5 and a hydrophobic patch on the surface of GSK-3β indicated in beige.

Notably, the peptide adopts a very similar conformation to that of the free peptide. Thus, the RMSD between the free L803 (see, FIG. 3) and the bound L803 is only 1.7 Å for all non-hydrogen atoms. It however moves away from the starting position and its Pro5 interacts with a hydrophobic surface patch of GSK-3β formed by residues Val214, Ile217 and the aromatic ring of Tyr216. Ala6 of L803, located at the phosphorylation site, is found 10.1 Å away from the ATP γ-phosphate, too far for phosphorylation.

In line with the experimental results (see, Example 1 hereinabove and FIG. 2), Phe93 of GSK-3β interacts with Pro8 of L803, Gln89 and Asn95 of GSK-3β are not involved in L803 binding and the charged residues of the peptide are solvent exposed. Gln9 of L803 is near GSK-3β residue Val214 and contacts it in parts of the trajectory, yet in every case the polar end of its side chain is exposed.

Previous studies of the interaction between pCREB and GSK3-β revealed that the two helical segments of the substrate bind in the deep groove next to the P-loop and a shallower groove near Phe93 [Ilouz et al. (2006) supra] (see, inset in FIG. 4). The experimental results do not rule out binding of L803 in the shallow groove. The MD simulation was therefore repeated using this as a starting position.

The most abundant structure in the last 1 ns of the simulation involves hydrophilic interactions between the charged residues of the peptide and GSK-3β; Phe93 in this model makes no contact with the inhibitor (see, FIG. 5). This result refutes the alternative binding mode of L803 in the shallow groove of GSK-3β.

Example 3

Newly Designed GSK-3 Inhibitors

The L803 binding model shows a contact between GSK-3 Phe93 and Pro8 and to a lesser extent Pro11 of L803 (see, FIG. 4). It was thus suggested that additional contacts with Phe93 may improve the inhibition. MD simulations with the variant L803F, in which a Phe residue was added at the C-terminus, as set forth in SEQ ID NO:11, were therefore performed.

FIG. 6A presents a representative model from the largest cluster in the MD simulation showing the binding geometry of L803F. The results show that L803F has a very similar conformation to L803 and it interacts extensively with Phe93 via its Pro8 and Phe12, and with the hydrophobic surface patch of GSK-3β.

Thus, in vitro kinase assays were performed with GSK-3β in the presence of L803 or L803F (200 μM each). The results are presented in FIG. 6B and show that the new peptide, L803F, has improved inhibition ability by about 50% relatively to L803. Percentage of the substrate phosphorylation obtained without inhibitor was defined as 100% (Con), and results are means of two independent experiments ±SEM.

In vitro kinase assays were also performed with GSK-3β in the presence of L803 or L803F at increasing concentrations and the results are presented in FIG. 7, further indicating the improved activity exhibited by L803F. Substrate phosphorylation obtained without inhibitor was defined as 100%, and results are means of two independent experiments ±SEM.

In an additional assay, human neuroblastoma SH-SY5Y cells, were treated with L803-mts (as set forth in SEQ ID NO:5) or L803F-mts (as set forth in SEQ ID NO:12) (20 or 40 μM) for 5 hours. Cells were collected and lysed in ice-cold buffer G (20 mM Tris pH 7.5, 10 mM β-glycerophosphate, 10% glycerol, 1 mM EGTA, 1 mM EDTA, 50 mM NaF, 5 mM sodium pyrophosphate, 0.5 mM orthovanadate, 1 mM benzamidine, 5 μg/ml leupeptin, 25 μg/ml aprotinin, 5 μg/ml pepstatin, and 0.5% Triton X100). Equal amounts of proteins (30 μg) were subjected to gel electrophoresis, transferred to nitrocellulose membranes, and immunoblotted with the anti-β-catenin antibody or anti-phospho-HSF-1 antibody (heat shock factor-1)(ser 303). FIG. 8 presents the β-catenin levels and phosphorylation levels of HSF-1 (ser 303) as determined by Western blot analysis using specific antibodies, with non-treated cells indicated as control (Con).

The elevation in β-catenin levels as presented in FIG. 8 is indicative for the ability of L803F-mts to inhibit GSK-3 at cellular conditions. In addition, it is shown in FIG. 8 that L803F-mts also reduced the phosphorylation levels of HSF-1 at HSF-1-GSK-3-phosphorylation site, serine 303, providing an additional evidence of its ability to inhibit cellular GSK-3.

In an addition assay, the interaction of L803F with the hydrophobic surface patch of GSK-3 was evaluated. The hydrophobic surface patch that consists of Val214, the aromatic ring of Tyr216 and Ile217, was predicted to contribute to the binding of L803 and L803F (see, FIGS. 4, 5 and 6A). The binding to this patch was therefore tested.

To this effect, a new mutant, V214A, as set forth in SEQ ID NO:13, in which Val214 of GSK-3β was mutated to alanine, was prepared, using the same method described hereinabove for other GSK-3 mutants. Val214 was shown to make multiple contacts with Pro5 of L803 and is highly exposed (60% exposure). Ile217 is far less exposed (23%), and mutation of Tyr216 hampers the kinase function of GSK-3β. In vitro kinase assays were performed with WT GSK-3β or the V214A mutant in the presence of L803 and L803F (250 μM each), using pIRS-1 as a substrate. The results, shown in FIG. 9, present the percentages of substrate phosphorylation obtained with the inhibitor versus those of phosphorylation obtained without the inhibitor (Con, defined as 100%) and are means of two independent experiments ±SEM. It was found that the ability of L803 and L803F to inhibit V214A was significantly impaired (about 20-25% reduction). These results support the existence of hydrophobic contacts between L803 and L803F and GSK-3β Val214.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A polypeptide consisting of the amino acid sequence of the formula

[Y$_n$ . . . Y$_1$]ZX$_1$X$_2$X$_3$S(p)W$_1$F wherein the polypeptide consists of 10 to 13 amino acid residues and optionally comprises a hydrophobic moiety attached thereto;
wherein,
   n is an integer from 3 to 6;
   S(p) is a phosphorylated serine residue or a phosphorylated threonine residue;
   Z is any amino acid residue except serine residue or threonine residue; and
   X$_1$-X$_3$, Y$_n$-Y$_1$ and W$_1$ are each independently any amino acid residue, wherein at least one of X$_1$ and X$_2$ is proline.

2. The polypeptide of claim 1, wherein W$_1$ is proline.

3. The polypeptide of claim 1, wherein S(p) is phosphorylated serine.

4. The polypeptide of claim 1, wherein Z is an alanine residue.

5. The polypeptide of claim 1, wherein X$_1$ and X$_2$ are each a proline residue.

6. The polypeptide of claim 5, wherein X$_3$ is a glutamine residue.

7. The polypeptide of claim 1, wherein n is 5.

8. The polypeptide of claim 7, wherein Y$_5$-Y$_1$ consists of the amino acid sequence Lys-Glu-Ala-Pro-Pro as set forth in SEQ ID NO: 17.

9. The polypeptide of claim 1, wherein the polypeptide comprises the amino acid sequence as set forth in SEQ ID NO: 11.

10. The polypeptide of claim 1, wherein the hydrophobic moiety is selected from the group consisting of a fatty acid and a fatty acid attached to an amino acid residue.

11. The polypeptide of claim 10, wherein the polypeptide consists of the amino acid sequence as set forth in SEQ ID NO: 12.

12. A pharmaceutical composition comprising, as an active ingredient, the polypeptide of claim 1, and a pharmaceutically acceptable carrier.

13. The pharmaceutical composition of claim 12, packaged in a packaging material and identified in print, on or in said packaging material, for use in the treatment of a biological condition associated with GSK-3 activity.

14. The composition of claim 13, wherein said biological condition is selected from the group consisting of obesity, non-insulin dependent diabetes mellitus, an insulin-dependent condition, an affective disorder, a neurodegenerative disease, a neurodegenerative disorder, a psychotic disease, a psychotic disorder, a cardiovascular disease, a cardiovascular disorder, a condition associated with a pathogenic parasite, and a condition treatable by stem cell transplantation.

15. A method of inhibiting an activity of GSK-3, the method comprising contacting cells expressing GSK-3 with an effective amount of the polypeptide of claim 1.

16. The method of claim 15, wherein said activity is a phosphorylation activity and/or an autophosphorylation activity.

17. A method of treating a biological condition associated with GSK-3 activity, the method comprising administering to a subject having the biological condition a therapeutically effective amount of the polypeptide of claim 1.

18. The method of claim 17, wherein said biological condition is selected from the group consisting of obesity, non-insulin dependent diabetes mellitus, an insulin-dependent condition, an affective disorder, a neurodegenerative disease, a neurodegenerative disease disorder, a psychotic disease, a psychotic disorder, a cardiovascular disease, a cardiovascular disorder, a condition associated with a pathogenic parasite, and a condition treatable by stem cell transplantation.

19. The method of claim 17, wherein said biological condition is selected from the group consisting of obesity, non-insulin dependent diabetes mellitus, an insulin-dependent condition, an affective disorder, a neurodegenerative disease, a neurodegenerative disorder, a psychotic disease, a psychotic disorder, a cardiovascular disease, a cardiovascular disorder, a condition associated with a pathogenic parasite, and a condition treatable by stem cell transplantation.

20. A polypeptide consisting of the amino acid sequence of the formula $$[Y_n \ldots Y_1]ZX_1X_2X_3S(p)W_1W_2,$$

wherein the polypeptide consists of 10 to 13 amino acid residues and optionally comprises a fatty acid attached thereto;

wherein, n is an integer from 3 to 6;

S(p) is a phosphorylated serine residue or a phosphorylated threonine residue;

Z is any amino acid residue except serine residue or threonine residue;

$X_1$-$X_3$ and $Y_n$-$Y_1$ are each independently any amino acid residue, wherein at least one of $X_1$ and $X_2$ is proline;

$W_1$ is any amino acid residue; and $W_2$ is an aromatic amino acid residue.

21. The peptide of claim 20, wherein $W_1$ is a proline residue.

22. The peptide of claim 20, wherein S(p) is phosphorylated serine.

23. The peptide of claim 20, wherein Z is an alanine residue.

24. A pharmaceutical composition comprising, as an active ingredient, the polypeptide of claim 20, and a pharmaceutically acceptable carrier.

25. The pharmaceutical composition of claim 24, packaged in a packaging material and identified in print, on or in said packaging material, for use in the treatment of a biological condition associated with GSK-3 activity.

26. The composition of claim 25, wherein said biological condition is selected from the group consisting of obesity, non-insulin dependent diabetes mellitus, an insulin-dependent condition, an affective disorder, a neurodegenerative disease, a neurodegenerative disorder, a psychotic disease, a psychotic disorder, a cardiovascular disease, a cardiovascular disorder, a condition associated with a pathogenic parasite, and a condition treatable by stem cell transplantation.

27. A method of inhibiting an activity of GSK-3, the method comprising contacting cells expressing GSK-3 with an effective amount of the polypeptide of claim 20.

28. A method of treating a biological condition associated with GSK-3 activity, the method comprising administering to a subject having the biological condition a therapeutically effective amount of the polypeptide of claim 20.

* * * * *

SEQUENCE LISTING

```
<160> NUMBER OF SEQ ID NOS: 18

<210> SEQ ID NO 1
<211> LENGTH: 433
<212> TYPE: PRT
<213> ORGANISM: Homo sapiens

<400> SEQUENCE: 1

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60
```

```
Gly Ser Phe Gly Val Val Tyr Gln Ala Lys Leu Cys Asp Ser Gly Glu
 65                  70                  75                  80

Leu Val Ala Ile Lys Val Leu Gln Asp Lys Arg Phe Lys Asn Arg
             85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
            115                 120                 125

Asn Leu Val Leu Asp Tyr Val Pro Glu Thr Val Tyr Arg Val Ala Arg
130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
            195                 200                 205

Arg Gly Glu Pro Asn Val Ser Tyr Ile Cys Ser Arg Tyr Tyr Arg Ala
210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
            275                 280                 285

Thr Glu Phe Lys Phe Pro Gln Ile Lys Ala His Pro Trp Thr Lys Asp
290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
            355                 360                 365

Thr Pro Ala Leu Phe Asn Phe Thr Thr Gln Glu Leu Ser Ser Asn Pro
370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr

<210> SEQ ID NO 2
<211> LENGTH: 7
<212> TYPE: PRT
<213> ORGANISM: Homo sapiens
<220> FEATURE:
<221> NAME/KEY: misc_feature
```

```
<223> OTHER INFORMATION: GSK-3 beta loop coresponding to amino acid
      residues 89-95

<400> SEQUENCE: 2

Gln Asp Lys Arg Phe Lys Asn
1               5

<210> SEQ ID NO 3
<211> LENGTH: 5
<212> TYPE: PRT
<213> ORGANISM: Artificial sequence
<220> FEATURE:
<223> OTHER INFORMATION: GSK-3 recognition motif
<220> FEATURE:
<221> NAME/KEY: misc_feature
<222> LOCATION: (1)..(1)
<223> OTHER INFORMATION: Can be Serine or Threonine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(4)
<223> OTHER INFORMATION: Can be any amino acid
<220> FEATURE:
<221> NAME/KEY: misc_feature
<222> LOCATION: (5)..(5)
<223> OTHER INFORMATION: Can be Serine or Threonine
<220> FEATURE:
<221> NAME/KEY: misc_feature
<222> LOCATION: (5)..(5)
<223> OTHER INFORMATION: A phosohrylated residue

<400> SEQUENCE: 3

Xaa Xaa Xaa Xaa Xaa
1               5

<210> SEQ ID NO 4
<211> LENGTH: 11
<212> TYPE: PRT
<213> ORGANISM: Artificial sequence
<220> FEATURE:
<223> OTHER INFORMATION: Substrate competitive inhibitor, L803
<220> FEATURE:
<221> NAME/KEY: misc_feature
<222> LOCATION: (10)..(10)
<223> OTHER INFORMATION: A phosphorylated residue

<400> SEQUENCE: 4

Lys Glu Ala Pro Pro Ala Pro Pro Gln Ser Pro
1               5                   10

<210> SEQ ID NO 5
<211> LENGTH: 12
<212> TYPE: PRT
<213> ORGANISM: Artificial sequence
<220> FEATURE:
<223> OTHER INFORMATION: Substrate competitive inhibitor, L803-mts
<220> FEATURE:
<221> NAME/KEY: misc_feature
<223> OTHER INFORMATION: N- terminally myristoylated
<220> FEATURE:
<221> NAME/KEY: misc_feature
<222> LOCATION: (11)..(11)
<223> OTHER INFORMATION: A phosohrylated residue

<400> SEQUENCE: 5

Gly Lys Glu Ala Pro Pro Ala Pro Pro Gln Ser Pro
1               5                   10
```

-continued

```
<210> SEQ ID NO 6
<211> LENGTH: 433
<212> TYPE: PRT
<213> ORGANISM: Artificial sequence
<220> FEATURE:
<223> OTHER INFORMATION: GSK-3 beta, D90A mutant

<400> SEQUENCE: 6

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Ala Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
```

```
                370             375             380
Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr

<210> SEQ ID NO 7
<211> LENGTH: 433
<212> TYPE: PRT
<213> ORGANISM: Artificial sequence
<220> FEATURE:
<223> OTHER INFORMATION: GSK-3 beta, K91A mutant

<400> SEQUENCE: 7

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
                20                  25                  30

Asp Gly Ser Lys Val Thr Thr Val Val Ala Thr Pro Gly Gln Gly Pro
            35                  40                  45

Asp Arg Pro Gln Glu Val Ser Tyr Thr Asp Thr Lys Val Ile Gly Asn
        50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Ala Arg Phe Lys Asn Arg
                85                  90                  95

Glu Leu Gln Ile Met Arg Lys Leu Asp His Cys Asn Ile Val Arg Leu
                100                 105                 110

Arg Tyr Phe Phe Tyr Ser Ser Gly Glu Lys Lys Asp Glu Val Tyr Leu
            115                 120                 125

Asn Leu Val Leu Asp Tyr Val Pro Glu Thr Val Tyr Arg Val Ala Arg
        130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
290                 295                 300
```

-continued

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
            325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
            405                 410                 415

Asp Arg Gly Gln Thr Asn Asn Ala Ala Ser Ala Ser Ala Ser Asn Ser
            420                 425                 430

Thr

<210> SEQ ID NO 8
<211> LENGTH: 433
<212> TYPE: PRT
<213> ORGANISM: Artificial sequence
<220> FEATURE:
<223> OTHER INFORMATION: GSK-3 beta, R92A mutant

<400> SEQUENCE: 8

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Ala Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

```
Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
            245                 250                 255

Phe Pro Gly Asp Ser Gly Val Asp Gln Leu Val Glu Ile Ile Lys Val
        260                 265                 270

Leu Gly Thr Pro Thr Arg Glu Gln Ile Arg Glu Met Asn Pro Asn Tyr
    275                 280                 285

Thr Glu Phe Lys Phe Pro Gln Ile Lys Ala His Pro Trp Thr Lys Asp
290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr

<210> SEQ ID NO 9
<211> LENGTH: 433
<212> TYPE: PRT
<213> ORGANISM: Artificial sequence
<220> FEATURE:
<223> OTHER INFORMATION: GSK-3 beta, F93A mutant

<400> SEQUENCE: 9

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Ala Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
```

```
                145                 150                 155                 160
Tyr Met Tyr Gln Leu Phe Arg Ser Leu Ala Tyr Ile His Ser Phe Gly
                165                 170                 175
Ile Cys His Arg Asp Ile Lys Pro Gln Asn Leu Leu Leu Asp Pro Asp
                180                 185                 190
Thr Ala Val Leu Lys Leu Cys Asp Phe Gly Ser Ala Lys Gln Leu Val
                195                 200                 205
Arg Gly Glu Pro Asn Val Ser Tyr Ile Cys Ser Arg Tyr Tyr Arg Ala
                210                 215                 220
Pro Glu Leu Ile Phe Gly Ala Thr Asp Tyr Thr Ser Ser Ile Asp Val
225                 230                 235                 240
Trp Ser Ala Gly Cys Val Leu Ala Glu Leu Leu Leu Gly Gln Pro Ile
                245                 250                 255
Phe Pro Gly Asp Ser Gly Val Asp Gln Leu Val Glu Ile Ile Lys Val
                260                 265                 270
Leu Gly Thr Pro Thr Arg Glu Gln Ile Arg Glu Met Asn Pro Asn Tyr
                275                 280                 285
Thr Glu Phe Lys Phe Pro Gln Ile Lys Ala His Pro Trp Thr Lys Asp
                290                 295                 300
Ser Ser Gly Thr Gly His Phe Thr Ser Gly Val Arg Val Phe Arg Pro
305                 310                 315                 320
Arg Thr Pro Pro Glu Ala Ile Ala Leu Cys Ser Arg Leu Leu Glu Tyr
                325                 330                 335
Thr Pro Thr Ala Arg Leu Thr Pro Leu Glu Ala Cys Ala His Ser Phe
                340                 345                 350
Phe Asp Glu Leu Arg Asp Pro Asn Val Lys Leu Pro Asn Gly Arg Asp
                355                 360                 365
Thr Pro Ala Leu Phe Asn Phe Thr Thr Gln Glu Leu Ser Ser Asn Pro
                370                 375                 380
Pro Leu Ala Thr Ile Leu Ile Pro Pro His Ala Arg Ile Gln Ala Ala
385                 390                 395                 400
Ala Ser Thr Pro Thr Asn Ala Thr Ala Ala Ser Asp Ala Asn Thr Gly
                405                 410                 415
Asp Arg Gly Gln Thr Asn Asn Ala Ala Ser Ala Ser Ala Ser Asn Ser
                420                 425                 430
Thr

<210> SEQ ID NO 10
<211> LENGTH: 433
<212> TYPE: PRT
<213> ORGANISM: Artificial sequence
<220> FEATURE:
<223> OTHER INFORMATION: GSK-3 beta, K94A mutant

<400> SEQUENCE: 10

Met Ser Gly Arg Pro Arg Thr Thr Ser Phe Ala Glu Ser Cys Lys Pro
1               5                   10                  15
Val Gln Gln Pro Ser Ala Phe Gly Ser Met Lys Val Ser Arg Asp Lys
                20                  25                  30
Asp Gly Ser Lys Val Thr Thr Val Val Ala Thr Pro Gly Gln Gly Pro
                35                  40                  45
Asp Arg Pro Gln Glu Val Ser Tyr Thr Asp Thr Lys Val Ile Gly Asn
                50                  55                  60
Gly Ser Phe Gly Val Val Tyr Gln Ala Lys Leu Cys Asp Ser Gly Glu
65                  70                  75                  80
```

Leu Val Ala Ile Lys Lys Val Leu Gln Asp Lys Arg Phe Ala Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Gly Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr

<210> SEQ ID NO 11
<211> LENGTH: 12
<212> TYPE: PRT
<213> ORGANISM: Artificial sequence
<220> FEATURE:
<223> OTHER INFORMATION: L803F synthetic peptide
<220> FEATURE:
<221> NAME/KEY: misc_feature
<222> LOCATION: (10)..(10)

```
<223> OTHER INFORMATION: A phosphorylated residue

<400> SEQUENCE: 11

Lys Glu Ala Pro Pro Ala Pro Pro Gln Ser Pro Phe
1               5                   10

<210> SEQ ID NO 12
<211> LENGTH: 13
<212> TYPE: PRT
<213> ORGANISM: Artificial sequence
<220> FEATURE:
<223> OTHER INFORMATION: L803F-mts synthetic peptide
<220> FEATURE:
<221> NAME/KEY: misc_feature
<223> OTHER INFORMATION: N- terminally myristoylated
<220> FEATURE:
<221> NAME/KEY: misc_feature
<222> LOCATION: (10)..(10)
<223> OTHER INFORMATION: A phosphorylated residue
<220> FEATURE:
<221> NAME/KEY: misc_feature
<222> LOCATION: (11)..(11)
<223> OTHER INFORMATION: A phosphorylated residue

<400> SEQUENCE: 12

Gly Lys Glu Ala Pro Pro Ala Pro Pro Gln Ser Pro Phe
1               5                   10

<210> SEQ ID NO 13
<211> LENGTH: 433
<212> TYPE: PRT
<213> ORGANISM: Artificial sequence
<220> FEATURE:
<223> OTHER INFORMATION: GSK-3 beta, V214A mutant

<400> SEQUENCE: 13

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205
```

-continued

```
Arg Gly Glu Pro Asn Ala Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr

<210> SEQ ID NO 14
<211> LENGTH: 9
<212> TYPE: PRT
<213> ORGANISM: Artificial sequence
<220> FEATURE:
<223> OTHER INFORMATION: p9CREB synthetic peptide
<220> FEATURE:
<221> NAME/KEY: misc_feature
<222> LOCATION: (7)..(7)
<223> OTHER INFORMATION: A phosphorylated residue

<400> SEQUENCE: 14

Ile Leu Ser Arg Arg Pro Ser Tyr Arg
1               5

<210> SEQ ID NO 15
<211> LENGTH: 14
<212> TYPE: PRT
<213> ORGANISM: Artificial sequence
<220> FEATURE:
<223> OTHER INFORMATION: pIRS-1 synthetic peptide
<220> FEATURE:
<221> NAME/KEY: misc_feature
<222> LOCATION: (11)..(11)
<223> OTHER INFORMATION: A phosphorylated residue

<400> SEQUENCE: 15

Arg Arg Glu Gly Gly Met Ser Arg Pro Ala Ser Val Asp Gly
1               5                   10
```

```
<210> SEQ ID NO 16
<211> LENGTH: 26
<212> TYPE: PRT
<213> ORGANISM: Artificial sequence
<220> FEATURE:
<223> OTHER INFORMATION: PGS-1 synthetic peptide
<220> FEATURE:
<221> NAME/KEY: misc_feature
<222> LOCATION: (21)..(21)
<223> OTHER INFORMATION: A phospohrylated residue

<400> SEQUENCE: 16

Tyr Arg Arg Ala Ala Val Pro Pro Ser Pro Ser Leu Ser Arg His Ser
1               5                   10                  15

Ser Pro Ser Gln Ser Glu Asp Glu Glu Glu
            20                  25

<210> SEQ ID NO 17
<211> LENGTH: 5
<212> TYPE: PRT
<213> ORGANISM: Artificial Sequence
<220> FEATURE:
<223> OTHER INFORMATION: short peptide

<400> SEQUENCE: 17

Lys Glu Ala Pro Pro
1               5

<210> SEQ ID NO 18
<211> LENGTH: 10
<212> TYPE: PRT
<213> ORGANISM: Artificial Sequence
<220> FEATURE:
<223> OTHER INFORMATION: 89-95 binding subsite of GSK-3

<400> SEQUENCE: 18

Leu Gln Asp Lys Arg Phe Lys Asn Arg Glu
1               5                   10
```